(12) United States Patent
Davis Sanberg et al.

(10) Patent No.: US 8,574,640 B2
(45) Date of Patent: **\*Nov. 5, 2013**

(54) COMBINED EFFECTS OF NUTRIENTS ON PROLIFERATION OF STEM CELLS

(75) Inventors: Cyndy Davis Sanberg, Spring Hill, FL (US); Paula Bickford, Ruskin, FL (US); Paul Sanberg, Spring Hill, FL (US); Jun Tan, Tampa, FL (US); R. Douglas Shytle, Lutz, FL (US)

(73) Assignees: University of South Florida, Tampa, FL (US); The Department of Veterans Affairs, Washington, DC (US); Natura Therapeutics, Inc., Tampa, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/901,329

(22) Filed: Oct. 8, 2010

(65) Prior Publication Data
US 2011/0038963 A1     Feb. 17, 2011

Related U.S. Application Data

(63) Continuation of application No. 12/288,848, filed on Oct. 23, 2008, now abandoned, which is a continuation of application No. 11/415,907, filed on May 2, 2006, now Pat. No. 7,442,394.

(60) Provisional application No. 60/676,733, filed on May 2, 2005.

(51) Int. Cl.
*A61K 36/82* (2006.01)
*A61K 36/45* (2006.01)
*A61K 38/00* (2006.01)
*A23L 1/30* (2006.01)

(52) U.S. Cl.
USPC ............... 424/729; 424/732; 426/73; 514/19

(58) Field of Classification Search
None
See application file for complete search history.

(56) References Cited

U.S. PATENT DOCUMENTS

| | | | |
|---|---|---|---|
| 6,080,431 A | 6/2000 | Andon et al. | |
| 6,440,450 B1 | 8/2002 | Han et al. | |
| 6,572,899 B1 * | 6/2003 | Gorsek | 424/732 |
| 6,602,526 B2 * | 8/2003 | Riley | 424/776 |
| 6,814,961 B1 | 11/2004 | Jensen et al. | |
| 2003/0059471 A1 | 3/2003 | Compton et al. | |
| 2004/0146539 A1 * | 7/2004 | Gupta | 424/401 |
| 2004/0219274 A1 | 11/2004 | Cook | |
| 2006/0275512 A1 | 12/2006 | Davis Sanberg et al. | |
| 2007/0110731 A1 | 5/2007 | Riley | |
| 2007/0116696 A1 * | 5/2007 | Riley | 424/94.5 |
| 2010/0272790 A1 * | 10/2010 | Morariu | 424/450 |

OTHER PUBLICATIONS

Adamson, John W. et al , Treatment of the Anemia of Chronic Renal Failure with Recombinant Human Erythropoietin, Annu. Rev. Med. (1990) vol. 41, pp. 349-360.
Asahara, Takayuki et al., Bone Marrow Origin of Endothelial Progenitor Cells Responsible for Postnatal Vasculogenesis in Physiological and Pathological Neovascularization, Circ. Res. (1999) vol. 85, pp. 221-228.
Baldauf, Kathrin et al , Influence of EGF/bFGF Treatment on Proliferation, Early Neurogenesis and Infarct Volume after Transient Focal Ischemia, Brain Research (2005) vol. 1056, pp. 158-167.
Bickford, Paula C. et al, Antioxidant-rich Diets Improve Cerebellar Physiology and Motor Learning in Aged Rats, Brain Research (2000) vol. 866, pp. 211-217.
Bickford, Paula C. et al., Nutraceuticals Synergistically Promote Proliferation of Human Stem Cells, Stem Cells and Development (2006) vol. 15, pp. 118-123.
Bizon, J. L. et al., Neurogenesis in a Rat Model of Age-Related Cognitive Decline, Aging Cell (2004) pp. 227-234.
Borlongan, Cesario V. et al., Glial Cell Survival is Enhanced During Melatonin-Induced Neuroprotection against Cerebral Ischemia, The FASEB Journal (2000) vol. 14, pp. 1307-1317.
Cao, Guohua et al., Antioxidant Capacity of Tea and Common Vegetables, J. Agric. Food Chem. (1996) vol. 44, pp. 3426-3431.
Cao, Guohua et al., Hyperoxia-induced Changes in Antioxidant Capacity and the Effect of Dietary Antioxidants, downloaded from www.jap.org on Oct. 22, 2007, pp. 1817-1822.
Cartford, M. Claire et al., Eighteen-Month-Old Fischer 344 Rats Fed a Spinach-Enriched Diet Show Improved Delay Classical Eyeblink Conditioning and Reduced Expression of Tumor Necrosis Factor α (TNFα) and TNFβ in the Cerebellum, The Journal of Neuroscience (2002) vol. 22, pp. 5813-5816.
Casadesus, Gemma et al., Qualitative Versus Quantitative Caloric Intake: Are they Equivalent Paths to Successful Aging?, Neurobiology of Aging (2002) vol. 23, pp. 747-769.
Casadesus, Gemma et al., Modulation of Hippocampal Plasticity and Cognitive Behavior by Short-Term Blueberry Supplementation in Aged Rats, Nutritional Neuroscience (2004) vol. 7, No. 5/6, pp. 309-316.

(Continued)

*Primary Examiner* — Chris R Tate
*Assistant Examiner* — Deborah Davis
(74) *Attorney, Agent, or Firm* — Bryan Cave LLP

(57) ABSTRACT

A method and composition for stimulating the proliferation and differentiation of stem cells is used to self-repair injury in mammals. A supplement is administered having an effective dose of blueberry, carnosine, catechin, green tea extract, Vita-Blue, Vitamin D3 or combinations of these. For example, a therapeutic amount of two or more of the supplements may be selected having a synergistic effect, allowing a lower dose to achieve the same or greater effective protection as a higher dose of any one of the supplements.

4 Claims, 14 Drawing Sheets

(56) References Cited

OTHER PUBLICATIONS

Chen, Zong Ping et al., Green Tea Epigallocatechin Gallate shows a Pronounced Growth Inhibitory Effect on Cancerous Cells but not on their Normal Counterparts, Cancer Letters (1998) vol. 129, pp. 173-179.
Conboy, Irina M. et al., Rejuvenation of Aged Progenitor Cells by Exposure to a Young Systemic Environment, Nature (2005) vol. 433, pp. 760-764.
Demetri, George D. et al., Granulocyte Colony-Stimulating Factor and Its Receptor, Blood (1991) vol. 78, No. 11, pp. 2791-2808.
Dimmeler, Stefanie et al., Aging of Progenitor Cells: Limitation for Regenerative Capacity?, Journal of the American College of Cardiology (2003) vol. 42, No. 12, pp. 2081-2082.
Drapeau, Elodie et al., Spatial Memory Performances of Aged Rats in the Water Maze Predict Levels of Hippocampal Neurogenesis, PNAS (2003) vol. 100, No. 24, pp. 14385-14390.
Gemma, Carmelina et al., Diets Enriched in Foods with High Antioxidant Activity Reverse Age-Induced Decreases in Cerebellar β-Adrenergic Function and Increases in Proinflammatory Cytokines, The Journal of Neuroscience (2002) vol. 22, pp. 6114-6120.
Henschler, R. et al., Maintenance of Transplantation Potential in Ex Vivo Expanded CD34+-Selected Human Peripheral Blood Progenitor Cells, Blood (1994) vol. 84, No. 9, pp. 2898-2903.
Hill, Jonathan M. et al, Circulating Endothelial Progenitor Cells, Vascular Function, and Cardiovascular Risk, The New England Journal of Medicine (2003) vol. 348(7), pp. 593-600.
Hisha, Hiroko et al., Isolation and Identification of Hematopoietic Stem Cell-Stimulating Substances From Kampo (Japanese Herbal) Medicine, Juzen-Taiho-To, Blood (1997) vol. 90, No. 3, pp. 1022-1030.
Hisha, Hiroko et al., Treatment of Shwachman Syndrome by Japanese Herbal Medicine (Juzen-Taiho-To): Stimulatory Effects of Its Fatty Acids on Hemopoiesis in Patients, Stem Cells (2002) vol. 20, pp. 311-319.
Holehouse, Ellen L. et al., Oliec Acid Distribution in Small Intestinal Epithelial Cells Expressing Intestinal-Fatty Acid Binding Protein, Biochimica et Biophysica Acta (1998) 1390, pp. 52-64.
Holliday, R. et al., A Role for Carnosine in Cellular Maintenance, Biochemistry (2000) vol. 65, No. 7, pp. 843-848.
Joseph, James A. et al., Reversals of Age-Related Declines in Neuronal Signal Transduction, Cognitive, and Motor Behavioral Deficits with Blueberry, Spinach, or Strawberry Dietary Supplementation, The Journal of Neuroscience (1999) vol. 19(18), pp. 8114-8121.
Koury, Mark J. et al., New Insights into Erythropoiesis: The Roles of Folate, Vitamin B12, and Iron, Annu. Rev. Nutr. (2004) vol. 24, pp. 105-131.
Kuhn, H. Georg et al., Neurogenesis in the Dentate Gyrus of the Adult Rat: Age-Related Decrease of Neuronal Progenitor Proliferation, The Journal of Neuroscience (1996) vol. 16(6), pp. 2027-2033.
Laufs, Ulrich et al., Physical Training Increases Endothelial Progenitor Cells, Inhibits Neointima Formation, and Enhances Angiogenesis, Circulation (2004) vol. 109(2), pp. 220-226.
Manach, Claudine et al., Bioavailability and Bioefficacy of Polyphenols in Humans. I. Review of 97 Bioavailability Studies, Am J. Clin. Nutr. (2005) vol. 81, pp. 230S-242S.
Mathieu, Chantal et al., Vitamin D and 1,25-dihydroxyvitamin D3 as Modulators in the Immune System, Journal of Steroid Biochemistry & Molecular Biology (2004) vol. 89-90, pp. 449-452.
Mazza, G. et al., Absorption and Anthocyanins from Blueberries and Serum Antioxidant Status in Human Subjects, J. Agric. Food Chem. (2002) vol. 50, pp. 7731-7737.
Meyer, Catherine, Scientists Probe Role of Vitamin D, JAMA (2004) vol. 292, No. 12, pp. 1416-1418.
Miller, Cindy L. et al., Expansion in vitro of Adult Murine Hematopoietic Stem Cells with Transplantable Lympho-Myeloid Reconstituting Ability, Proc. Natl. Acad. Sci. (1997) vol. 94, pp. 13648-13653.
Munro, I., Derivation of Tolerable Upper Intake Levels of Nutrients, American Journal of Clinical Nutrition (2001) vol. 74, pp. 862-867.
Ogawa, Makio, Differentiation and Proliferation of Hematopoietic Stem Cells, Blood (1993) vol. 81, No. 11, pp. 2844-2853.
Park, Young Joon et al., Quantitation of Carnosine in Humans Plasma after Dietary Consumption of Beef, J. Agric. Food Chem. (2005) vol. 53, pp. 4736-4739.
Passamonti, Sabina et al., Fast Access of Some Grape Pigments to the Brain, J. Agric. Food Chem. (2005) vol. 53, pp. 7029-7034.
Penn, Marc S. et al., Role of Stem Cell Homing in Myocardial Regeneration, Intl. Journal of Cardiology (2004) vol. 95 Suppl. 1, pp. S23-S25.
Prickaerts, Jos et al., Learning and Adult Neurogenesis: Survival with or without Proliferation?, Neurobiology of Learning and Memory (2004) vol. 81, pp. 1-11.
Semba, Richard D. et al., T Cell Subsets and Mortality in Older Community-Dwelling Women, Experimental Gerontology (2005) vol. 40, pp. 81-87.
Socolovsky, Merav et al., Cytokines in Hematopoiesis: Specificity and Redundancy in Receptor Function, Advances in Protein Chemistry (1998) vol. 52, pp. 141-198.
Song, Dong Up et al., Effect of Drinking Green Tea on Age-Associated Accumulation of Maillard-Type Fluorescence and Carbonyl Groups in Rat Aortic and Skin Collagen, Archives of Biochemistry and Biophysics (2002) vol. 397, No. 2, pp. 424-429.
Vasa, Mariuca et al., Number and Migratory Activity of Circulating Endothelial Progenitor Cells Inversely Correlate with Risk Factors for Coronary Artery Disease, Circulation Research (2001) vol. 89, pp. E1-7.
Vieth, Reinhold et al., Efficacy and Safety of Vitamin D3 Intake Exceeding the Lowest Observed Adverse Effect Level1-3, Am. J. Clin. Nutr. (2001) vol. 73, pp. 288-294.
Vieth, Reinhold, Why the Optimal Requirement for Vitamin D3 is probably much higher than what is officially recommended for Adults, The Journal of Steroid Biochemistry & Molecular Biology (2004) vol. 89-90, pp. 575-579.
Wang, Y-C. et al., The Specific Anti-Cancer Activity of Green Tea (−)-epigallocatechin-3-gallate (EGCG), Amino Acids (2002) vol. 22, pp. 131-143.
Whetton, Anthony D. et al., Role of Cytokines and Extracellular matrix in the regulation of Haemopoietic stem cells, Current Opinion in Cell Biology (1998) vol. 10(6), pp. 721-726.
Williams, Robert J. et al., Serial Review: Flavonoids and Isoflavones (Phytoestrogens): Absorption, Metabolism, and Bioactivity, Free Radical Biology & Medicine (2004) vol. 36, No. 7, pp. 838-849.
Willis, Lauren et al., Blueberry Extract Enhances Survival of Intraocular Hippocampal Transplants, Cell Transplantation (2005) vol. 14, pp. 213-223.
Web page for Life Extension.

* cited by examiner

FIGURE 3

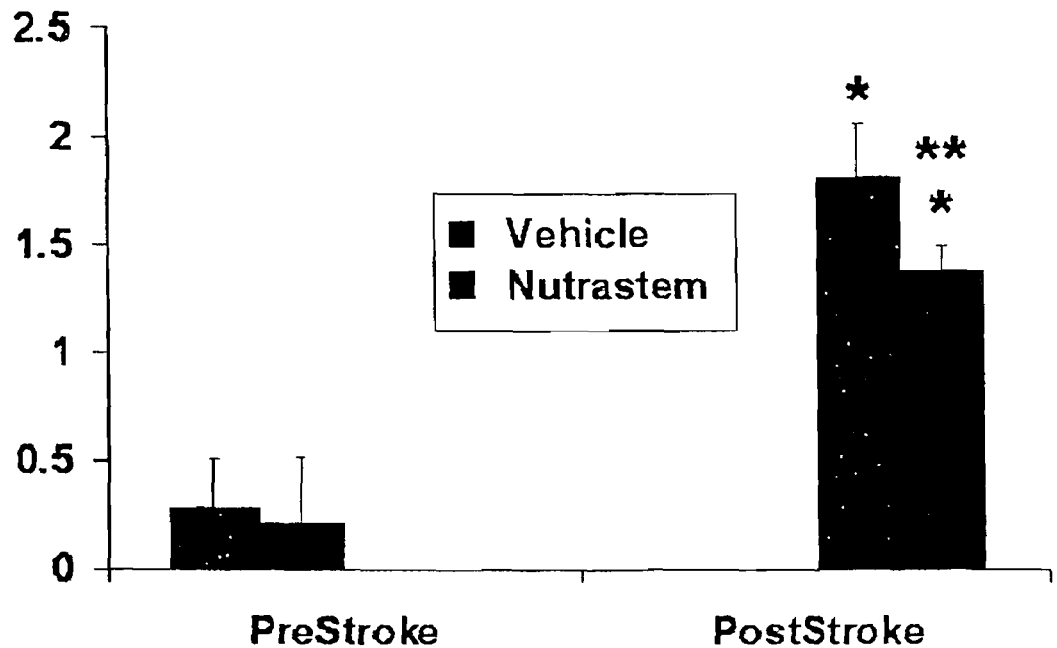
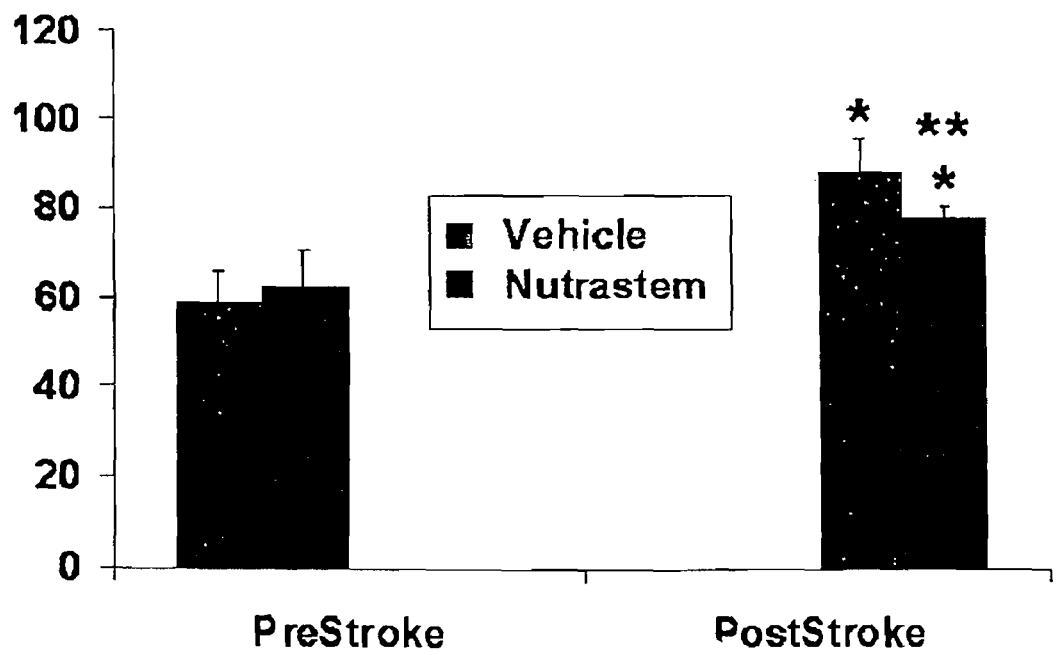
FIG. 8

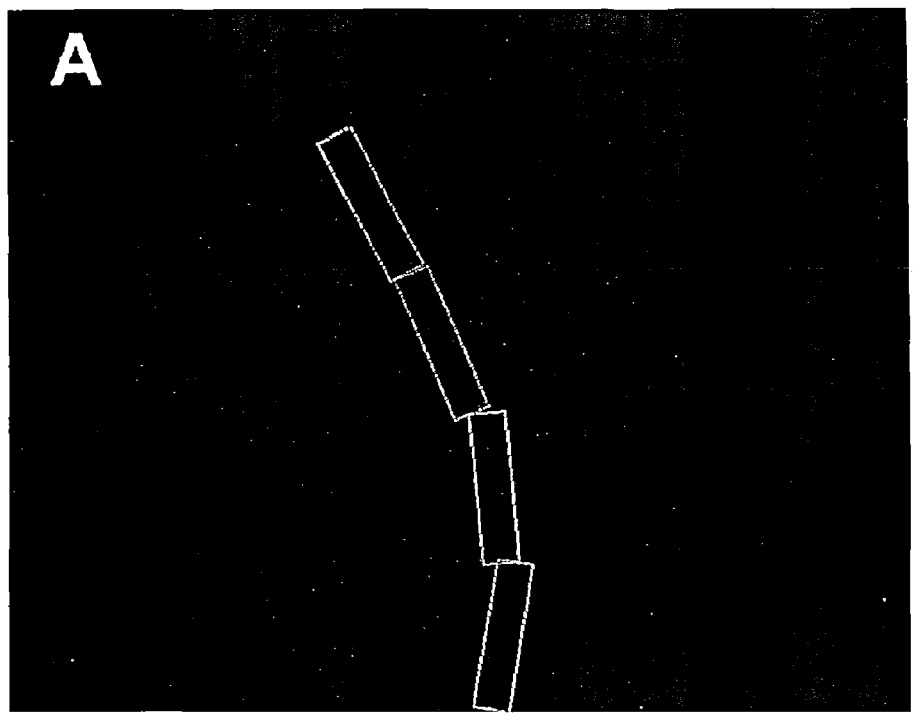
FIG. 11
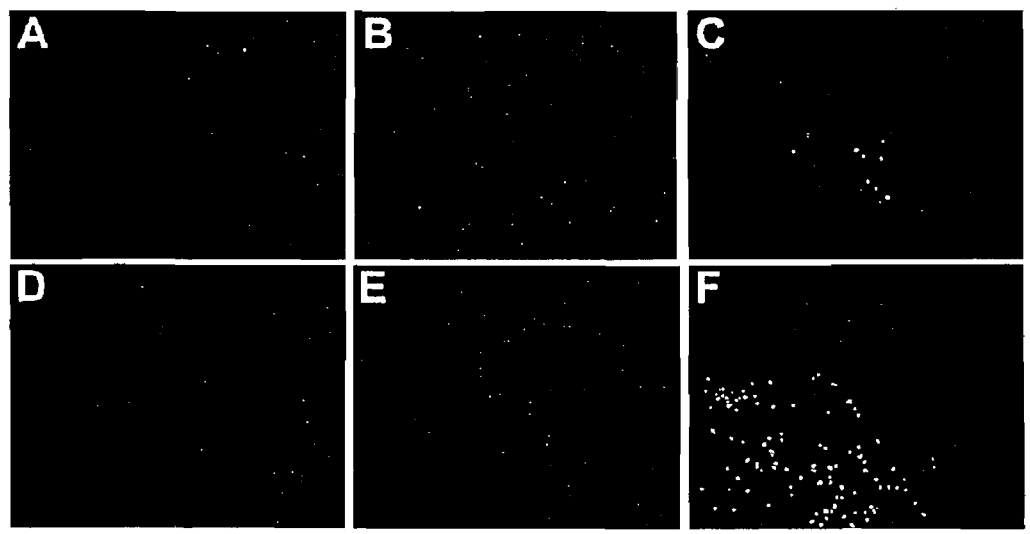
FIGS. 13 A-F

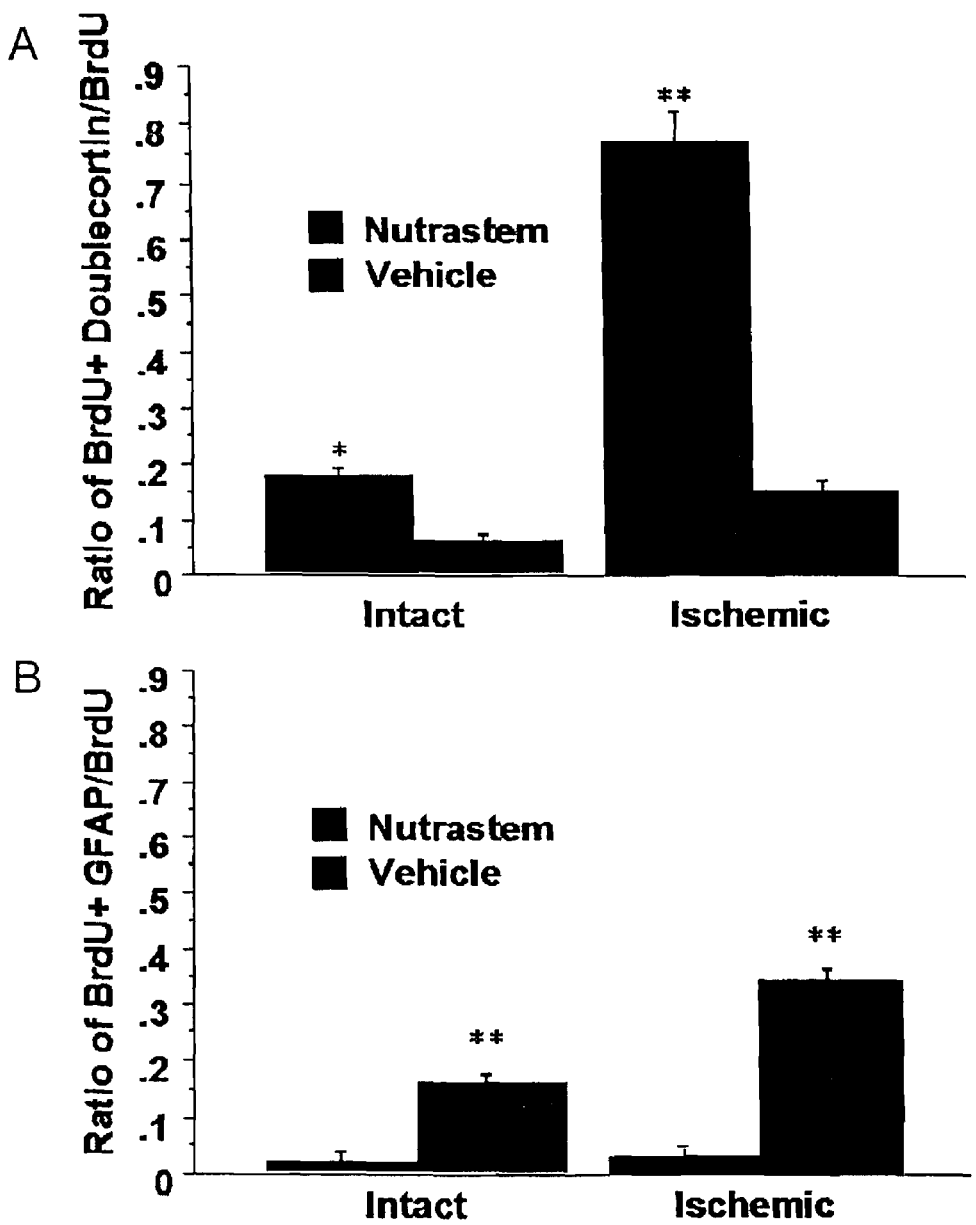
FIGS. 14 A,B

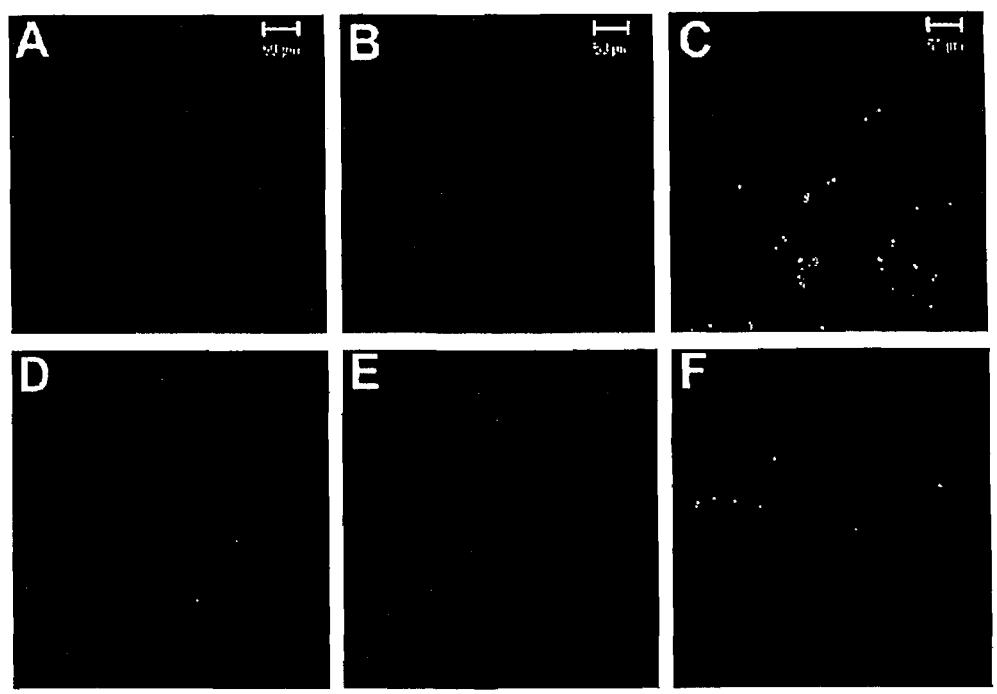
FIGS. 15 A-F

COMBINED EFFECTS OF NUTRIENTS ON PROLIFERATION OF STEM CELLS

RELATED APPLICATIONS

This application claims the benefit of the filing date of U.S. Patent Application No. 60/676,733 filed May 2, 2005 to Sanberg, et al., the disclosure of which is hereby incorporated herein by reference.

BACKGROUND OF THE INVENTION

Stem cells are found in many organs of the adult human including bone marrow, peripheral blood, umbilical cord blood, spleen, tooth pulp, and brain. These progenitor cells are being investigated for their potential use as transplanted tissues in the treatment of diseases such as cancer, diabetes, stroke, amyotrophic lateral sclerosis (ALS) and Parkinson's disease. Little effort however is being directed toward enhancing the endogenous stem cells in the adult as an avenue to promote healing. In many of these diseases, and in aging, stem cells and progenitors are known to have a reduced proliferative activity. For example, neural stem cells, muscle satellite cells, and endothelial progenitors all show reduced proliferation in the aged and may play a role in pathology of age-associated diseases (Kuhn et al., 1996; Conboy et al., 2005; Dimmeler and Vasa-Nicotera, 2003). In cardiovascular disease, for example, there is a correlation between a reduction in peripheral blood endothelial progenitor cells and many risk factors for cardiovascular disease (Vasa et al., 2001; Hill et al., 2003). As many of the diseases being targeted by stem cell therapies are age-associated diseases, selecting nutritional strategies that increase stem cell proliferation in the aged population seems appropriate.

Hematopoietic stem cells (HSCs) have been investigated for many years for their utility in cancer treatments. Experimental investigations of hematopoiesis and clinical approaches to correcting its deficiencies have focused on cytokine activity. Cytokines modulate hematopoiesis by maintaining the self-renewal of stem cells and stimulating the proliferation and maturation of committed progenitor cells required for the continuous replacement of mature blood cells (Ogawa 1993; Socolovsky et al. 1998; Whetton and Spooncer 1998).

In vitro, various combinations of cytokines including interleukin-1 (IL-1), IL-3, IL-6, stem cell factor (SCF), and erythropoietin (EPO) have been found to support the growth of multipotent progenitor cells (Henschler et al. 1994; Miller and Eaves 1997). Individually, granulocyte-colony-stimulating factor (G-CSF) and EPO are growth factors for committed myeloid and erythroid progenitors, respectively (Demetri and Griffin 1991). Clinically, G-CSF and EPO provide effective treatments for neutropenia and anemia (Adamson and Eschbach 1990; Eschbach et al. 1990) and are used to enhance peripheral blood progenitors as an alternative to bone marrow transplantation for cancer patients. However, such treatments are costly, and are not without certain risks.

Decreases in hematopoietic and endothelial progenitors are associated with aging. Decreases in certain hematopoietic progenitors has been reported in frail aging women (Semba et al., 2005). Endothelial progenitor cells (EPC) are also derived from bone marrow and found in the circulating blood. Circulating EPC's home to sites of neovascularization and injury (Penn et al., 2004) and can then differentiate into mature endothelial cells (Asahara et al., 1999). Declines in EPC's are noted in patients with coronary artery disease (Vasa et al., 2001), and when isolated from patients with high risk factors for coronary artery disease, show increased senescence in vitro (Hill et al., 2003). It has been suggested that endothelial progenitors play a role in cardiovascular homeostasis and that the decline observed in aging and disease tips the balance toward injury rather than repair. Exercise has been shown to increase EPC's and this may be one of the reasons that exercise has beneficial effects on cardiovascular disease (Laufs et al., 2004). Developing nutritional based strategies to increase progenitors could push the balance back towards repair, thus having a significant impact on health.

Neural stem cells also decline with aging (Kuhn et al., 1996) and some have postulated that declines in neurogenesis with aging are related to cognitive decline while others disagree (Bizon et al., 2004; Drapeau et al., 2003; Prickaerts et al., 2004). Nonetheless, it has been shown that nutritional treatments, such as feeding with blueberry, which improve cognitive function (Joseph et al., 1999) also increase neurogenesis (Casadesus et al., 2004). Thus, there is a correlation between improved neural stem cell proliferation and improved cognitive function.

While potentially better treatments are currently in development, few research studies have investigated the effects of natural products, vitamins, and other nutrients which may modulate self-renewal of stem cells. However, in recent years there has been an upsurge of interest on the effects of various dietary insufficiencies on hematopoietic and immune responsiveness. Folate, vitamin 1312, and iron have crucial roles in erythropoiesis. Erythroblasts require folate and vitamin B12 for proliferation during their differentiation. Deficiency of folate or vitamin B12 inhibits purine and thymidylate syntheses, impairs DNA synthesis, and causes erythroblast apoptosis, resulting in anemia from ineffective erythropoiesis (Koury and Ponka, 2004). Other studies have recently found that dietary fatty acids, particularly oleic acid and linolenic acid, actively promote the proliferation of hematopoietic stem cells (Hisha et al., 1997; Hisha et al., 2002) as well as modulate the self-renewal of intestinal epithelial cells (Holehouse et al., 1998). Vitamin D has also received increasing attention over the past few years, in part, because recent studies suggest that nearly half the US population may be vitamin D deficient (Meyer, 2004). Recent laboratory studies demonstrate that vitamin D3 has a dramatic effect on stimulating the proliferation of various forms of multipotent progenitor cells, particularly those involved with the immune system (Mathieu et al., 2004). Recent laboratory research on cellular senescence (the end of the life cycle of dividing cells) suggests that the dietary nutrient, carnosine, found in muscle and brain of mammals, has the remarkable ability to rejuvenate cells approaching senescence, restoring normal appearance and extending cellular life span (Hipkiss et al., 1998; Holliday and McFarland, 2000).

The use of fruits or vegetables has the benefit of providing a cocktail of many different phytochemicals with multiple actions including antioxidant and antiinflammatory effects and is one reason they have been extensively studied in the field of cancer biology. Other studies suggest dietary supplementation with foods high in antioxidants, such, as blueberries, can prevent and even reverse cellular and behavioral parameters that decline as a function of aging (Joseph et al., 1999; Gemma et al., 2002). For example, dietary supplementation with 2% blueberry extract has produced both neuroprotective and neurorestorative effects in aged animals, perhaps as a result of modulation of cell signaling cascades (Williams, Spencer et al. 2004). Furthermore, blueberry extract has been shown to increase neurogenesis in the aged rat brain (Casadesus, NSci Abstract, 2002). We have shown that feeding blueberries to aged rats increases the survival and growth of hippocampal grafts grown in the anterior chamber of the eye (Willis et al., 2005), demonstrating that nutritional supplementation can not only increase proliferation of tissues, but promote appropriate differentiation.

Green tea is a drink made from the steamed and dried leaves of the Camellia sinensis plant, a shrub native to Asia. Green tea has been widely consumed in Japan, China, and other Asian nations to promote good health for at least 3,000 years. Recently, scientists have begun to study it's health effects in animal, laboratory, and observational human studies. Although active compounds within green tea extract have been shown to inhibit the growth of a number of tumor cell lines, they do not effect the growth of normal cells at similar concentrations (Chen et al., 1998; Wang and Bachrach, 2002) and actually may provide cellular protection from aging (Song et al., 2002).

In light of such findings reviewed above, it appears that certain nutrients, vitamins, and flavonoids could have important roles in maintaining the self-renewal of stem cells and stimulating the proliferation and differentiation of committed progenitors required for the continuous replacement of mature cells in the blood, brain, and other tissues. Furthermore, it may be possible to use certain natural products, either alone or synergistically, for the treatment of conditions where the stem cell replacement appears warranted such as aging or diseases associated with aging. However, the amounts of such substances that have shown actual results in studies are impractical to implement as supplementation to an ordinary diet. Even if studies are correct about the value of these substances, consumption of sufficient quantities to substantially improve health is impractical.

Aged mammals, such as rats, dogs and humans, can improve age-related declines in motor abnormalities and cognitive abnormalities with dietary interventions that include foods with a high antioxidant capacity. Antioxidants work at the cellular level; therefore, it would be expected that benefits of antioxidants in one mammal would be mirrored in other mammals. Certain foods were identified on the basis of the ability to show antioxidant activity in vivo in mammals and in an in vitro assay. Hundreds of foods were examined using this assay (Cao et al., 1997) and several were chosen with high in vitro antioxidant activity for testing in vivo. For example, when 18 month old rats are fed a diet in which 2% of the diet is a blueberry extract, after 2 months on this diet, we observe a significant improvement in motor performance on a balance beam (Joseph et al., 1999). We also observed a significant improvement on a Morris water maze in rats fed a diet supplemented with large quantities of strawberry, blueberry or spinach (Joseph et al., 1999). These same animals also show improved dopamine release in the striatum. A spinach diet improves age-induced deficits in motor learning using either a rod running motor learning task or classical eye blink conditioning (Bickford et al., 2000; Cartford et al., 2002). Markers of inflammation, such as the pro-inflammatory cytokine TNFα are increased in the brains of PD patients (Mogi et al., 1996), and 30 days following 6-OHDA lesions. We have shown that these diets decrease markers of oxidative damage and pro-inflammatory cytokines (Gemma et al., 2002; Cartford et al., 2002), furthermore these changes are related to the foods antioxidant activity as foods such as cucumber which are low in antioxidant activity have no effect (Gemma et al., 2002). We have been examining these diets in an animal model of Parkinson's disease. We have preliminary data showing that the blueberry or spirulina diet will increase the immune response 7 days following an insult and then prevent the prolonged activation of microglia at later time points. It is this later prolonged activation which we hypothesize is detrimental and reflects the ongoing inflammation observed in Parkinson's disease.

While benefits are known for incorporating antioxidants into the diet of humans, adjusting diets to incorporate a large proportion of these foods is difficult and often fails to incorporate sufficient amounts of antioxidants to make a significant difference on proliferation and differentiation of bone marrow cells, $CD34^+$ HSCs, $CD133^+$ progenitor cells from peripheral blood or any other stem cells. It would be of great benefit to identify certain natural compounds that can promote proliferation of hematopoietic stem cells or other stem cells, synergistically, such that the natural compounds could be taken in the form of a supplement that would have a significant, measurable effect.

BRIEF SUMMARY OF THE INVENTION

We have discovered that certain natural products, when combined, exert a synergistic proliferation of human bone marrow cells, CD34+, and CD133+ progenitors. A method of increasing stem cell proliferation and, in some cases, selective migration, and compositions have been found that synergistically increase the proliferation compared to individual foods, such that a combination of these natural substances shows a substantial effect with administration of small quantities of specific natural substances in mammals. Selecting at least three substances from the group of substances consisting of blueberry, camosine, catechin, green tea extract, and vitamin $D_3$, compounding the substances into a supplement easily digested in the digestive tract, and administering the substances to a mammal is shown to synergistically increase measurable indicators of proliferation of certain stem cells, protection against damage and/or damage repair mechanisms.

BRIEF DESCRIPTION OF DRAWINGS

Figure 3:
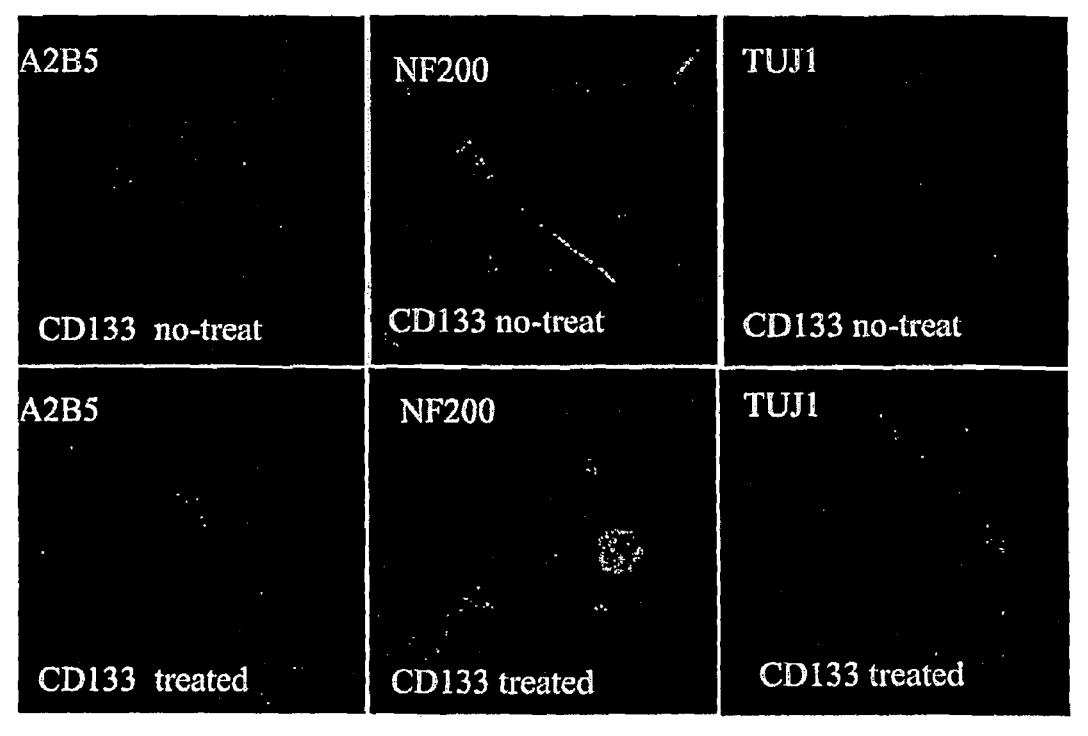

FIG. 3 shows the effect of green tea in differentiation of stem cells.

FIGS. 8, 9a-c show behavioral and histologic results for a test of one example of supplementation in mammals receiving supplementation versus a control group of animals.

FIGS. 10A-F, 11, 12A,B, 13A-F, 14A,B, 15A-F show test results for induced stroke tests.

The patent or application contains at least one drawing executed in color. Copies of this patent or patent application with color drawing(s) will be provided by the Office upon request and payment of the necessary fee.

DETAILED DISCLOSURE

Figure 1:
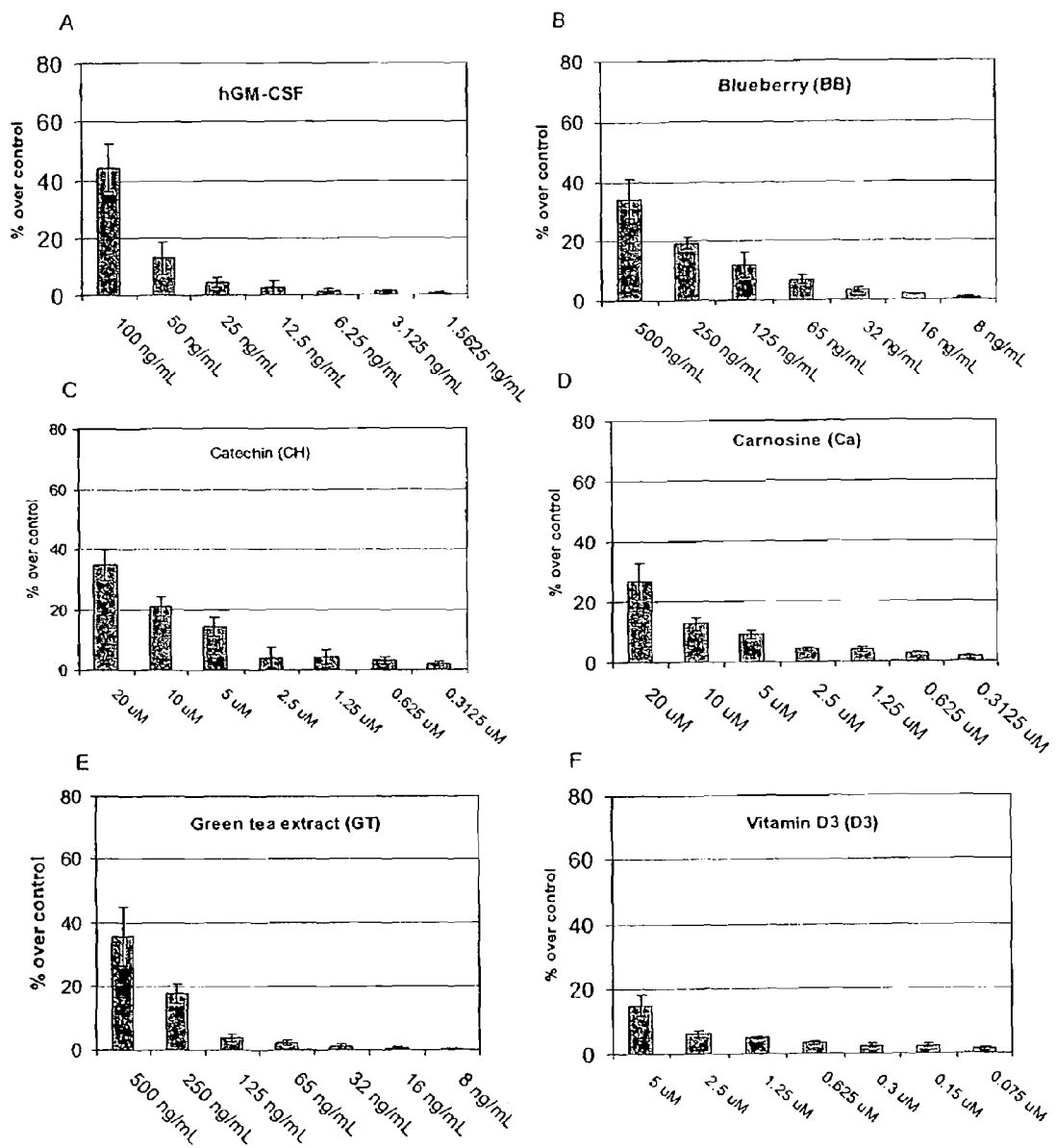
FIG. 1 shows data from a test of natural substances.

FIG. 1 shows the results of nutrition related substances, such as extracts and compounds, promote cell proliferation of human bone marrow cells in a dose-dependent manner. Human bone marrow cells were cultured in 96-well tissue-culture plates ($5\times10^4$/well) and treated with human granulocyte colony-stimulating factor (hGM-CSF; A, as positive), blueberry extract (B), catechin (C), carnosine (D), green tea extract (E) and vitamin D3 (F) at a wild range of doses as indicated for 72 hours. After the treatment, these cells were prepared for MTT analysis of cell proliferation described in Materials and Methods. Data were represented as the percentage over control (without any treatment under the same cultured condition). For A-F, ANOVA and post hoc testing shows significant differences of mean percentage over control (+/−SD with n=3 independent experiments) between high and low doses ($p<0.005$).

Three antioxidants were compared for protective effects against stroke in rats: blueberry, spinach and spirulina. Results show that each, in sufficient quantities in a diet, have a significant, differential effect on reducing ischemia-induced caspase-3 activity and cerebral infarction. Animals were put on a diet of either control, blueberry (10,000 mg/kg/day), spinach (10,000 mg/kg/day) or spirulina (1500 mg/kg/day) for 4 weeks prior to the insult. We used a 60 minute occlusion of the middle cerebral artery and at 24 hours examined the size of the infarct using TTC staining. We found a 70% protection in infarct size in the spirulina treated rats and a 50% protection in both the blueberry and spinach treated rats. In these animals we have observed a significant decrease in caspase-3 activity and the number of TUNEL positive cells indicating that a reduction of apoptosis was achieved. All groups also showed significant improvement on horizontal and vertical activity measures when compared with controls. However, the amount of antioxidant consumed per day makes it difficult to sustain the benefits of any of these diet plans long terms.

Figure 2:
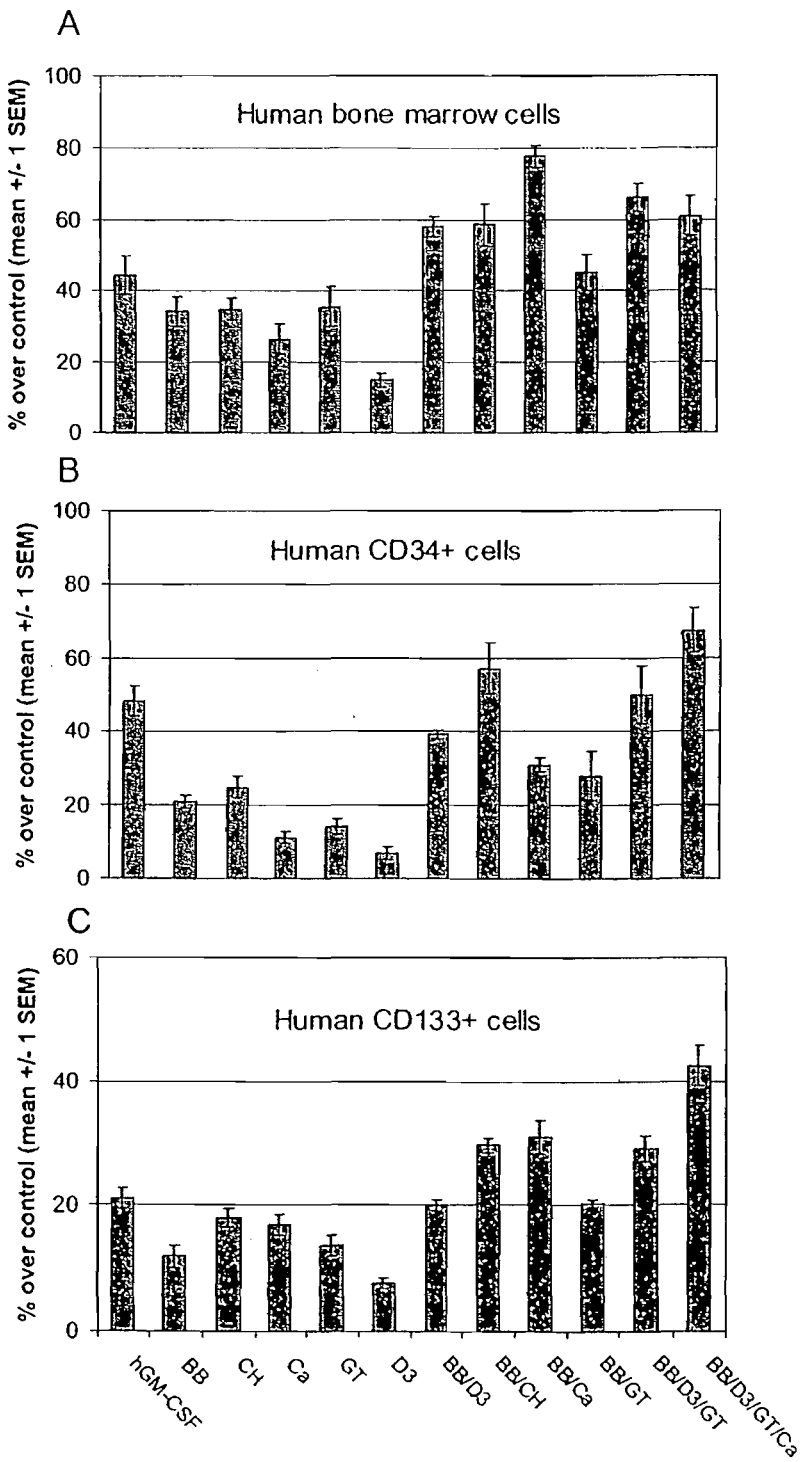
FIG. 2 shows a synergistic effect of a combination of natural ingredients.

FIG. 2 shows a Blueberry extract synergistically affects cell proliferation in the presence of co-treatment with D3, CH, D3/GT or D3/GT/Ca. In (A) Human bone marrow cells were cultured in 96-well tissue-culture plates ($5\times10^4$/well) and treated with blueberry extract (500 ng/mL) in the presence of D3 (5 μM), CH (20 μM), Ca (20 4M), GT (500 ng/mL), D3 (5 μM)/GT (500 ng/mL) or D3 (5 μM)/GT (500 ng/mL/Ca (20 μM) for 72 hours. In (B) Human bone marrow-derived CD34+ cells ($5\times10^4$/well)was treated as same above (A). For MTT assay, these cells were prepared for cell proliferation analysis. Data were also represented as the percentage over control. ANOVA and post hoc testing shows significant differences of mean percentage over control (+/−SD with n=3 independent experiment) between individual and certain combined treatments, for A, BB/D3 combined treatment compared to BB or D3 individual treatment ($p<0.005$), BB/CH compared to BB or CH ($p<0.005$), BB/Ca compared to BB or Ca ($p<0.001$), BB/D3/GT compared to BB, D3 or GT, BB/D3/GT/Ca compared to BB, D3, GT or Ca; for B, BB/CH combined treatment compared to BB or CH individual treatment ($p<0.005$), BB/D3/GT/Ca compared to BB, D3, GT or Ca ($p<0.001$). Human CD133+ cells were cultured for 23 days in the presence or absence of green tea (50 μg/ml). Cells were then fixed and stained for A2B5 Left panels (RED), NF200 middle panels (Green) or TUJ1 right panel (red). Nuclei were stained with DAPI (Blue). In both conditions there were some cells that were positive for all markers which is consistent with literature that has shown that CD133+ cells can differentiate into neural lineages. In the cells treated with green tea, the staining was significantly more prevalent.

Several whole food extracts, herbal extracts, and specific compounds were screened individually for proliferative activity on human bone marrow cells in culture. Spinach, spirulina, EGCG, epicatechin, withania, somnifera, carao, rehmania glutinosa, and astragulus membranaceous did not show high activity on proliferation of human bone marrow cells in culture and were not tested further.

Certain whole-food extracts, such as blueberry, green tea, and specific compounds, including catechin, carnosine, and vitamin D3, were found to increase cell proliferation of human bone marrow cells in a dose-dependent manner (FIG. 1B-F). Cell proliferation, as determined by MTT assay, is displayed as the percent of cell proliferation over the control, which represents cells cultured in the same condition without any extract or compound added.

The positive control, human granulocyte colony-stimulating factor (hGM-CSF; FIG. 1A), produced a 44.5±8.1% proliferation at the highest dose of 100 ng/ml. Blueberry and catechin demonstrated a 34.5±6.7 and 34.8±5.2% increase in proliferation at 500 ng/ml and 20±M, respectively (FIG. 1 B,C). Carnosine displayed a 26.6±6.0% increase at 20±M (FIG. 1 D), and vitamin D3 displayed a lower percentage of proliferation, 14.8±3.3% at 5±M (FIG. 1 F). Green tea produced a proliferation similar to blueberry and catechin with 35.6±9.2% proliferation at 500 ng/ml (FIG. 1 E).

Human bone marrow cells were cultured with different combinations of the extracts and compounds and with the individual extracts and compounds at the highest doses determined to promote the greatest amount of proliferation, which was represented by FIG. 1A-F. The positive control, hGM-CSF displayed 48.3±7.4% proliferation. As shown in FIG. 2A blueberry, catechin, carnosine, green tea, and vitamin D3, alone, did not cause proliferation in a significantly different manner from that shown in FIG. 1 A-F. However, the combination of extracts and compounds resulted in a greater percentage of proliferation than observed with the individual extracts and compounds. For example, blueberry/vitamin D3 exhibited a 62% increase in proliferation, blueberry/catechin a 70% increase, and blueberry/carnosine with the greatest synergistic affect of 83% (FIG. 2A). Blueberry/green tea, blueberry/vitamin D3/green tea, and blueberry/vitamin D3/green tea/carnosine also displayed significant increases in proliferation of 56%, 72%, and 70%, respectively, in FIG. 2A and significant synergistic effects are shown in FIGS. 2B and 2C, also.

Figure 4:
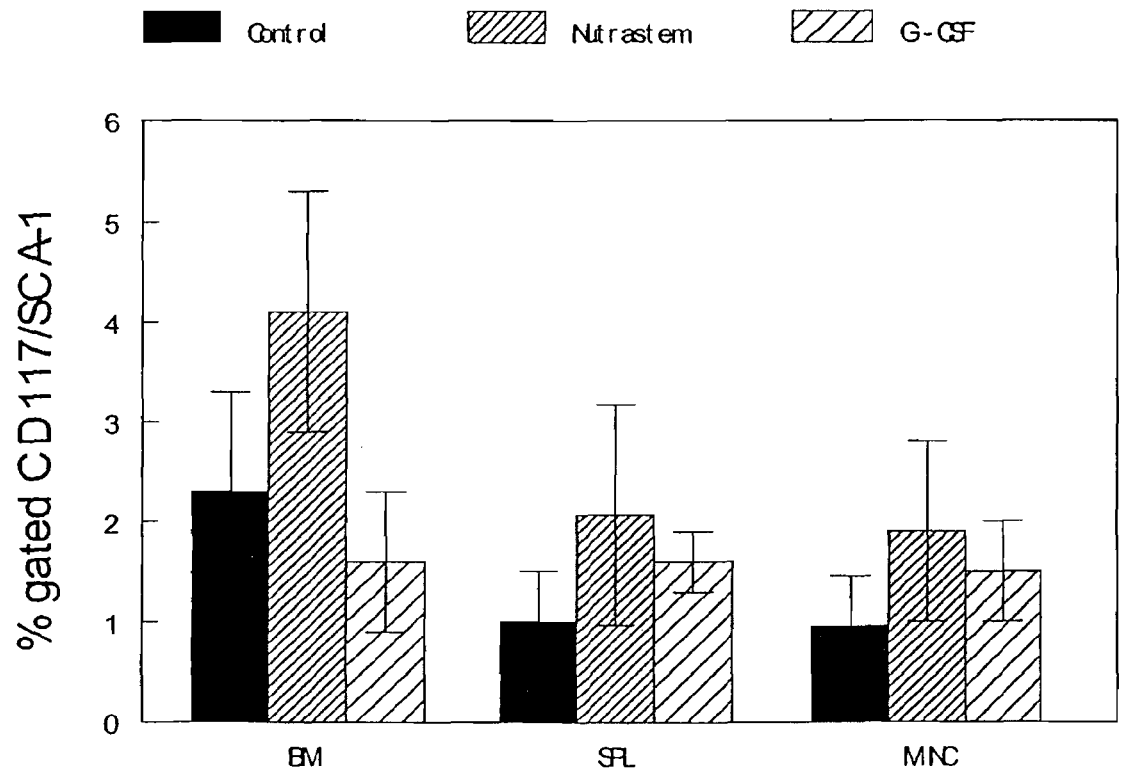
FIG. 4 shows the effects on certain organs of a mammal of a process for stem cell proliferation and differentiation in mammals.
Figure 5:
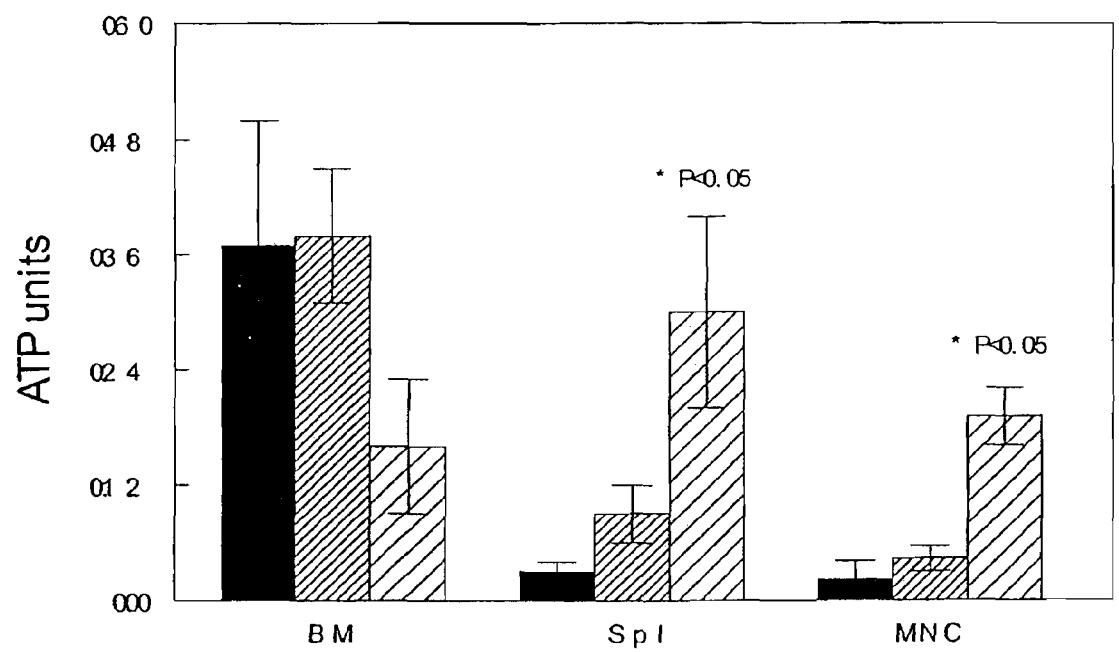
FIG. 5-7 show additional tests of stem cell proliferation and differentiation (FIG. 5) and protection against oxidative damage (FIGS. 6 and 7).

FIG. 4 shows results for bone marrow (BM), spleen (SPL) and the mononuclear fraction of peripheral blood (MNC) isolated from 3 mice treated with either water by gavage (control), a composition of synergistic natural substances by gavage (Composition 1 supplementation) or G-CSF i.p. (G-CSF) for 6 days. On day 7 cells were isolated and prepared for flow cytometry. The percentage of CD117/SCA-1 positive cells was analyzed. This represents a hematopoietic stem cells. As can be seen above, there was a trend for an increase in this population of cells in the mice given Composition 1 supplementation compared to all cell populations examined. In the G-CSF treated mice there was a trend for an increase in the spleen and MNC populations, but a decrease in the BM population which is consistent with what is observed for other progenitors following G-CSF assessed by the colony forming assay. FIG. 5 shows results for tests of bone marrow (BM), spleen (Spl), and mononuclear cells (MNC) isolated from mice treated with either water (control), G-CSF, or Composition 1 for 6 days. On day 7 cells were isolated and plated in the colony forming assay (see specific methods) for 5 days. ATP was detected by luciferase assay and luminescence was converted to ATP units with use of a standard curve. As can be seen from this graph GCSF has the expected effect to reduce bone marrow CFU's and increase CFU's found in both spleen and the MNC fraction. Composition 1 shows a trend towards increasing CFU's in both spleen and MNC fractions but does not reduce CFU's in the BM fraction. Although a statistically small sample, the effects show a cytokine like effect to reduce progenitors in the bone marrow.

Reagents. All compounds were added to cell cultures as described in the results sections. Sources of compounds were as follows: blueberry (freeze dried powder, Van Drunen Farms, Momence, Ill.), green tea extract (Rexall), Carnosine (Sigma), Catechin (Sigma), and the activated form of vitamin D3 (25-Hydroxycholeciferol, Sigma).

Cell Cultures and MTT Assay. For cell proliferation analysis, human bone marrow cells, human CD34$^+$ cells or CD133 cells (BioWhittaker, Inc.) were cultured in 96 well plates ($5 \times 10^4$/well) containing 100 µL of complete medium (RPMI 1640 medium supplemented with 5% fetal calf serum). These cells were treated for 72 hours with various extracts at a wide range of doses (8 ng/mL to 500 ng/mL) or molecular compounds (0.3125 µM to 20 µM). Five hours before the end of the treatment, 20 µL of MTT solution (MTT kit, Sigma) was added to each well. These plates were then incubated in a $CO_2$ incubator at 37° C. for 5 hours and the cultured media removed with needle and syringe. 200 µL of DMSO was added to each well with pipetting up and down to dissolve crystals. These plates were put back into the 37° C. incubator for 5 minutes, transferred to plate reader and measured absorbance at 550 nM. Data were represented as relative percentage mean proliferation, defined as O.D. reading number of each treated cells normalized to control cells (in the absence of treatment).

Promotion of Bone Marrow Cell Proliferation in a Dose-dependent Manner. Certain whole food extracts, such as Blueberry (BB), Green Tea (GT), and specific compounds, including Catechin (CH), Carnosine (Ca), and Vitamin D3 (D3), were found to increase cell proliferation of human bone marrow cells in a dose dependent manner (FIG. 1). Cell proliferation as determined by MTT assay is displayed as the percent of cell proliferation over the control, which represents cells cultured in the same condition without any extract or compound added. The positive control, human granulocyte colony-stimulating factor (hGM-CSF; FIG. 1A), produced a 44.5±8.1% proliferation at the highest dose of 100 ng/mL. Blueberry (BB) and CH demonstrated a 34.5±6.7 and 34.8±5.2% increase in proliferation at 500 ng/mL and 20 µM respectively (FIG. 1B, 1C). The compound, Ca displayed a 26.6±6.0 increase at 20 µM (FIG. 1D), and D3 displayed a lower percentage of proliferation, 14.8±3.3% at 5 µM (FIG. 1F). Green tea (GT) produced a proliferation similar to BB and CH with 35.6±9.2% proliferation at 500 ng/mL (FIG. 1E).

Synergistic Stimulatory Effect of Extracts and Compounds on Proliferation. To determine if the extracts and compounds displayed synergistic effect on cell proliferation, we cultured human bone marrow cells with different combinations of the extracts and compounds. We also cultured the bone marrow cells with the individual extracts and compounds at the highest doses determined to promote the greatest amount of proliferation, which was represented by FIG. 1A-F. The positive control, hGM-CSF displayed 48.3±7.4% proliferation, while BB, CH, Ca, GT, and D3 alone did not cause proliferation in a significantly different manner as demonstrated in FIG. 2A. However, the combination of extracts and compounds resulted in a greater percentage of proliferation than observed with the individual extracts and compounds. For example, BB/D3 exhibited a 62% increase in proliferation, BB/CH a 70% increase, and BB/Ca with the greatest synergistic affect of 83% (FIG. 2A). BB/GT, BB/D3/GT, and BB/D3/GT/Ca also displayed significant increases in proliferation of 56%, 72%, and 70% respectively (FIG. 2A).

Promotion of CD34$^+$ Cell Proliferation and Synergistic Properties of Extracts and Compounds. To determine whether these extracts and compounds promoted cell proliferation of other progenitor cells, we cultured CD34$^+$ human hematopoietic stem cells under the same conditions as the bone marrow cells using different combinations of the extracts and compounds, and with the individual extracts and compounds at the highest doses determined to promote the greatest amount of proliferation in the bone marrow cell studies, which was represented by FIG. 1A-F. The results revealed a 48.3±7.4 increase for hGM-CSF, which was approximately a 5% increase in proliferation as compared to hGM-CSF effect on the bone marrow cells (FIG. 2B). However, individually, BB, CH, Ca, GT, and D3 displayed a 20.9±3.0, 24.8±5.0, 11.05±2.1, 14.0±3.7 and 6.9±2.6 increase in proliferation respectively, which are much lower than observed in the bone marrow cells (FIG. 2B). However when combined, BB/D3, BB/CH, BB/Ca, BB/GT, and BB/D3/GT demonstrated a 39.3±2.0%, 57.3±10.4%, 30.9±3.4%, 27.9±10.0%, and 49.9±13.1% increase in proliferation respectively which is at least additive and in some synergistic (FIG. 2B). Interestingly, the combination of BB/D3/GT/Ca resulted in an increase of 67.6±11.9%, a simple additive effect would have been 52% demonstrating a synergistic (FIG. 2B).

Promotion of CD133+ Cell Proliferation and Synergistic Properties of Extracts and Compounds. Some of the compounds and combinations with the greatest activity on proliferation of the bone marrow derived CD34+ cells were then used to treat CD133+ (progenitor cells) collected from peripheral blood and cultured under the same conditions as above. Cell proliferation was determined by MTT Assay and is displayed as the percent of cell proliferation over the control. The results revealed an 21.11±2.9% increase after treatment with hGM-CSF (FIG. 2C). Individually, BB, Ca, GT, and D3 displayed a 11.9±3.1, 16.9±3.3, 13.57±3.0, 7.6±1.39% increase in proliferation respectively (FIG. 2C). When combined, BB/D3/GT, and BB/D3/GT/Ca demonstrated a 29.2±3.6 and 42.5±5.9% increases in proliferation (FIG. 2C) of human CD133$^+$ cells.

In vivo studies. We have initiated studies with Composition 1 administered by gavage to DBA mice. To date we have treated 3 mice with (Blueberry Extract: 3 mg/kg/day; Carnosine: 10 mg/kg/day; Vitamin D3: 1 mg/kg/day; green tea extract: 3 mg/kg/day) or water by gavage, in addition 3 mice have been treated with G-CSF 4 µg/mouse i.p.. Initial studies were done at 6 days of treatment as this is an optimal time for G-CSF to show mobilization of progenitors into the peripheral blood. Bone marrow, spleen and peripheral blood mononuclear cells were examined by flow cytometry with SCA-1 and CD117, the presence of both markers is indicative of multipotent hematopoietic stem cells. As can be seen in FIG. 4, there was in increase in CD117/SCA-1 double positive events in all 3 cell fractions examined in mice treated with Composition 1. A small increase was also observed following G-CSF. The three fractions were also assessed in the HALO™ colony forming assay. As can be seen in FIG. 5, G-CSF produced a decrease in colony forming units—total count (CFU-C's) in the bone marrow and an increase in CFU-C's in both spleen and mononuclear cells. This effect is consistent with the literature and thus increases our confidence in this version of the CFU-C assay. Our product at this dose and time of delivery showed a trend for an increase in CFU-C's in the spleen and MNC fraction. G-CSF is a potent cytokine used to increase progenitors for a short term effect; however administering G-CSF beyond a short term effect causes an ultimate decrease of bone marrow progenitors Our product is designed for longer term administration and does not show a long term decrease in bone marrow progenitors.

The results demonstrate that various natural compounds and their combinations promote the proliferation of human bone marrow, human bone marrow derived $CD34^+$, and human peripheral blood derived $CD133^+$ cells. When tested individually, these compounds were most effective in promoting proliferation of the bone marrow cells and less effective when used to treat the progenitor populations. This finding may reflect an effect of the individual compounds on the mature cell populations that are also present in the bone marrow cell cultures. When the activity of the compounds was examined in combinations, the additive and synergistic effects were more profound in the progenitor $CD34^+$ and $CD133^+$ cells. Surprisingly, some of the combinations tested resulted in proliferation which exceeded that produced by the positive control, hGM-CSF. For example, the combination of blueberry extract, green tea extract, carnosine, and vitamin D3 produced greater proliferation than that induced by hGM-CSF in all three cell types, with $CD133^+$ cells being most sensitive with a proliferation response twice that produced by hGM-CSF. Of all the compounds tested, blueberry extract most consistently produced significant proliferation when combined with the other compounds.

In summary, we demonstrated for the first time that certain natural compounds can promote proliferation of hematopoietic stem cells in vitro, and more specifically that a combination of blueberry extract, green tea extract, carnosine, and vitamin D3 demonstrate synergistic activity in these assays.

Following in vivo, extension of our promising in vitro results, it is likely that an oral formulation of blueberry extract, green tea extract, carnosine, and vitamin D3 developed as a dietary supplement could be used to promote healing naturally in various parts of the body where progenitor cells are in need, such as in the case with various disease states or with an injury.

Figure 6:
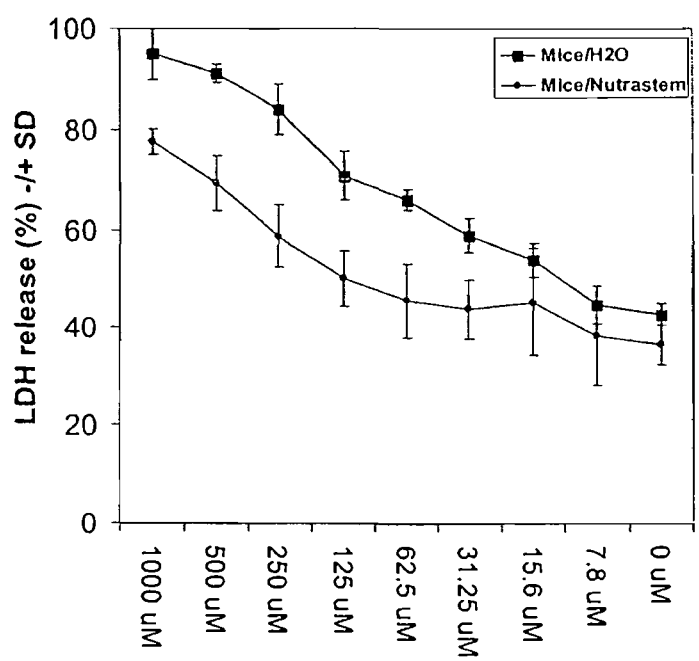
Figure 7:
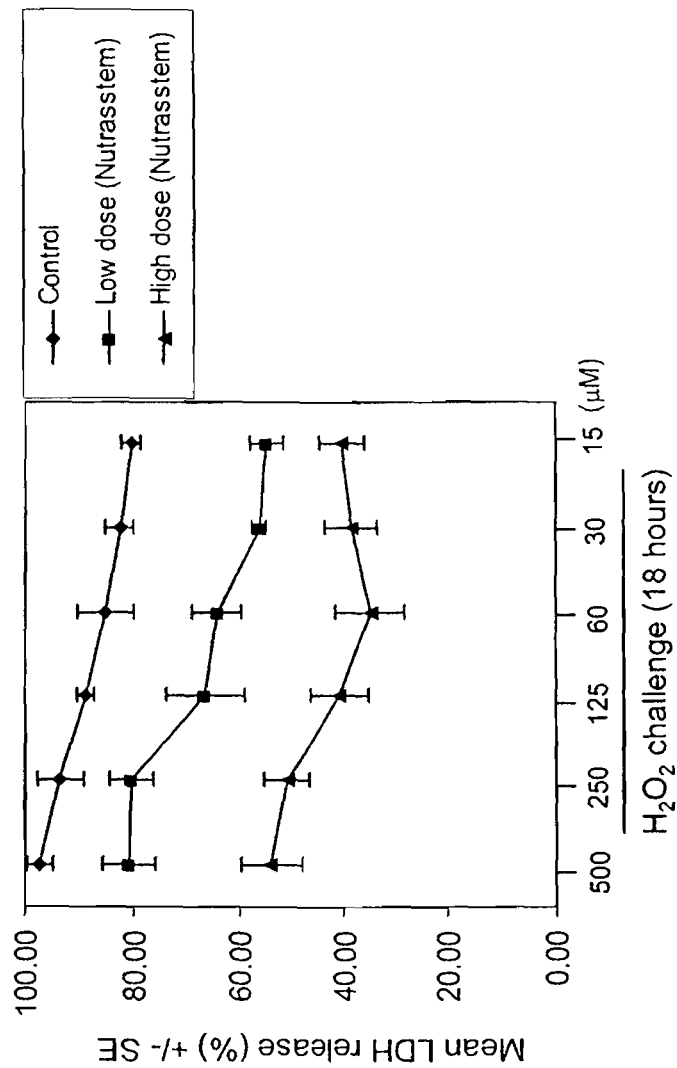

One of the ways of testing the effectiveness of an antioxidant is to show its effects in preventing oxidative damage, such as shown in FIGS. 6 and 7. Mice (BalbC) treated with supplementation for 2 weeks by gavage were anesthetized by using isoflurane in a bell jar. After being properly anesthetized both hind legs were then removed, at the pelvic joint, from the torso and placed in a Petri dish containing 70% ethanol. All tissue was then dissected away and removed from the bone, and femur and are isolated in another dish. A 1 cc syringe filled with 1 mL of culture media (minimum essential media) and is inserted through the endplate of the femur while the other end is removed using scissors. The bone marrow is then washed through the bone into another dish that contains 10 mL of culture media. The bone is washed several times to ensure sufficient marrow collection. This process is repeated for the fibia and samples from both legs are collected together and cell number was assessed using a hemacytometer. Cells were then cultured at 5×106 cells per well and incubated at 37° C. for 2 hrs. The bone marrow was challenged using a serial dilution of $H_2O_2$ ranging from 1000 µM-7.8 µM, and incubated over night at 37° C. The culture media was collected and centrifuged at 14,000 rpm for 10 min at 4° C. Supernatants were transferred to fresh tubes and the LDH levels were tested using the CytoTox 96 Non-Radioactive Cytotoxicity Assay (Promega) in strict accordance with the manufacturers' protocols. Results were then calculated to show the percent cell death for the control and treatment groups, using varying doses of peroxide (+/−SD) as the oxidant.

FIG. 6 shows data from a sample of 3 mice per group of BalbC mice treated with either water Composition 1. The drop in LDH release (in %) −/+SD (ordinate) is shown against the amount of oxidant used in µM (abscissa). As the amount of oxidant used increases, (from right to left), the amount of LDH released increases faster for the control group with water than for the group protected by Composition 1 In FIG. 7, results are shown for mice treated as described in the tests of FIG. 6. Composition 2 and 3 (see below) were administered for 2 weeks at 2 different doses. The first dose is exactly equivalent to the dose provided in a formulation for humans, and the higher dose is 10 fold increase, because the metabolism of a mouse is 10 times higher than humans. Thus the higher dose in the mouse will produce similar blood levels of components to the dose used in the formulation for humans, and the blood level is thought to be the significant measure of concentration in comparisons between mammals.

Composition 2 for the human formulation comprised Green tea of 5.7 mg/kg, Carnosine of 1.4 mg/kg, Vitamin D3 of 0.71 µg/kg, Blueberry=5.1 mg/kg, and Vitablue=0.6 mg/kg. The composition for the formulation needed to produce a similar blood level in mice was administered at 10 times the human formulation (Composition 3). Significant protection is provided at both doses compared to the control group. The human equivalent dose shows a marked protection against oxidative damage.

An example of a supplement formulation may include 360 mg of blueberry. Alternatively, an equivalent amount of VitaBlue may be added. It is thought that anthocyanins are the active ingredient in blueberries, and VitaBlue is enriched by ten times in anthocyanins compared to blueberry. Thus, it is believed that 40 mg of VitaBlue is equivalent to 400 mg of blueberry. A pharmacokinetic study (pK study) in humans [Mazza G, Kay C D, Cottrell T, Holub B J (2002) Absorption of Anthocyanins from Blueberries and Serum Antioxidant Status in Human Subjects J. Agric. Food Chem., 50, 7731-7737](7) found consumption of 1200 mg blueberry anthocyanins resulted in human plasma conc. of 17 ng/ml. The equivalent of 800 mg of blueberry (1.2% anthocyanins) would lead to a blood concentration of approximately 0.14 ng/ml anthocyanins by interpolation. The doses tested in vitro ranged from 0.08 to 5 ng/ml anthocyanins. In humans, this range corresponds to a dose in a range from 400 mg to 25 grams of blueberries and/or their equivalent. The upper range has been tested as a supplement in our tests for aging and other studies. In practical terms, 25 grams of blueberry would be about 12 pills, which is impractical for supplements provided in pill form. More preferably, the upper limit for blueberry and equivalents is about 5 grams per day. Even more preferably, blueberry is compounded with other supplements that provide a synergistic effect.

Our in vitro data for activity of green tea extract tested a range from 4 ng/ml to 250 ng/ml catechins (assuming only 10% of the catechins went into solution, we obtain a range of 0.4-25 ng/ml). A pK study in humans [Manach C, Gary Williamson, Christine Morand, Augustin Scalbert, and Christian Rèmèsy (2005) Bioavailability and bioefficacy of polyphenols in humans. I. Review of 97 bioavailability studies. *Am J Clin Nutr;* 81 (suppl):230S-42S](6) found that consumption of 500 mg catechins resulted in a plasma conc of 2 nmol/l. Using the MW of catechin at 280, 2 nmol/l=0.58 ng/ml. Thus, in humans 400 mg GTE will result in a 0.4 ng/ml plasma concentration, and a preferred range of green tea extract is from 400 mg to 25 grams. For practical considerations, the amount of green tea extract is selected to be no greater than 5 grams. More preferably, green tea extract is compounded with other substances to provide a synergistic effect.

In one example, Vitamin D3 is used as 2000 IU's, which is equivalent to 50 µg. In humans, daily administration of 4000

IUs (100 mcg) results in a blood concentration of 100 nmol/L. There is no official RDA for vitamin D3 [R. Vieth, D. Fraser, Vitamin D insufficiency: no recommended dietary allowance exists for this nutrient, CMAJ 166 (2002) 1541-1542](4). According to a conservative report of the Food and Nutrition Board [R. Vieth (2004) Why the optimal requirement for Vitamin D3 is probably much higher than what is officially recommended for adults. Journal of Steroid Biochemistry & Molecular Biology 89-90 (2004) 575-579], the safety limit (no adverse effect level, NOAEL) of vitamin D3 intake in humans is 60 mcg (or 2400 IU) per day [Standing Committee on the Scientific Evaluation of Dietary Reference Intakes. Dietary Reference Intakes: Calcium, Phosphorus, Magnesium, Vitamin D, and Fluoride. National Academy Press, 1997]. After applying a margin of safety, the recommended upper limit is 50 mcg (2000 IUs) per day for intake by the general public [I. Munro, Derivation of tolerable upper intake levels of nutrients, Am. J. Clin. Nutr. 74 (2001) 865-867]. Clinical trials show no benefit from oral doses 20 mcg (800 IUs) or less [R. Vieth (2004) Why the optimal requirement for Vitamin D3 is probably much higher than what is officially recommended for adults. Journal of Steroid Biochemistry & Molecular Biology 89-90 (2004) 575-579](1). Recent, clinical trials also report that human oral doses of 1000 IUs (20 mcg/day) to 4000 IUs (100 mcg/day) are completely safe and within normal levels produced by exposure to the sun (total body sun exposure=10,000 IUs/day) [R. Vieth (2004) Why the optimal requirement for Vitamin D3 is probably much higher than what is officially recommended for adults. Journal of Steroid Biochemistry & Molecular Biology 89-90 (2004) 575-579](1). A dose of 50 mcg leads to a plasma concentration of 0.05 µM. Doses tested in vitro ranged from 0.07 to 5 µM, a range of 50 µg to 5000 µg in humans, which is from 2000 IU to 20,000 IU. In practice, 20,000 IU's is beyond any limit recommended and might lead to hypercalcemia. In a preferred example, the range of Vitamin D3 is selected in a range from 2,000 to 4,000 IU.

In one example, carnosine is added to a supplement in a dose of 100 mg. A recent pK study in humans [Park Y J, Volpe S L, Decker, E A (2005) Quantitation of Carnosine in Humans Plasma after Dietary Consumption of Beef. J. Agric. Food Chem., 53, 4736-4739] found that two beef patties contain 250 mg carnosine and when ingested by humans resulted in a plasma conc. of 33 mg/l which peaked at 3 hrs and returned to baseline at 5 hrs. With a Mw of 266 and assuming 5 liters of blood in a human, 250 mg carnosine produces a blood conc of 620 µM. Assuming linear pK, 100 mg should produce a human blood concentration of 248 µM. Doses tested ranged from 1-20 µM, effect was still increasing at 20 µM. Thus, a dose as high as 620 may be helpful and still be within normal ranges for human consumption. A preferred effective range is about 10 mg to 100 mg of carnosine based on extrapolation from results obtained.

In one preferred example, at least three substances are selected to be compounded into a supplement tablet, pill, or other form for ease of administering a dose. In humans, a ratio of blueberry to Vitamin D3 may be selected from 400:0.1 to 1:4000 or 25,000:0.05 to 1:500,000, based on the previous maximum and minimum ranges for each. However, limiting the doses of each to 5 grams, yields ratios from 5,000:0.5 to 1:100,000 for the highest to lowest ranges of each component.

Similarly, a ratio may be calculated for blueberry to green tea. Thus, the lowest to highest ratio is in a range from 4:50 to 0.08:1, and the highest to lowest ratio is in a range from 50:4 to 12.5:1.

In another example, several ratios may be selected for a combination of blueberry to carnosine to green tea extract to Vitamin D3. Examples would include from 4,000:4,000:100:1, such as a composition having Vitamin D3 at the recommended highest level, or 100,000:100,000:2,000:1, with Vitamin D3 at its low level.

Two groups of adult male Sprague-Dawley rats initially received supplementation using Composition 1 (n=8) or vehicle (n=7). Composition 1 equals (blueberry 3 mg/kg/day; Vitamin D3 1 mg/kg/day; green tea 3 mg/kg/day; and carnosine 10 mg/kg/day. Dosing for Composition 1 and vehicle consisted of daily oral administration (using a gavage) over a two-week period.

We tested a pre-stroke diet supplementation dosing regimen using daily administration of supplementation for two weeks. Following the last supplementation, on day 14, all animals underwent a stroke surgery using a transient one-hour suture occlusion of middle cerebral artery (MCAo). This MCAo stroke model was used to test the neuro-protection of supplementation for some examples of the present invention. To reveal the functional effects of supplementation, animals are subjected to established behavioral tests just prior to stroke surgery and again on day 14 post-stroke. Behavioral tests include Bederson test and elevated body swing test (EBST), which are sensitive to stroke-induced motor and neurological deficits, respectively.

The Bederson test is conducted following the procedures previously described (Borlongan et al. 2004a,b). Neurologic score for each rat is obtained using 4 tests which include: (1) observation of spontaneous ipsilateral circling, graded from 0 (no circling) to 3 (continuous circling); (2) contralateral hindlimb retraction, which measures the ability of the animal to replace the hindlimb after it is displaced laterally by 2 to 3 cm, graded from 0 (immediate replacement) to 3 (replacement after minutes or no replacement); (3) beam walking ability, graded 0 for a rat that readily traverses a 2.4-cm-wide, 80-cm-long beam to 3 for a rat unable to stay on the beam for 10 seconds; and (4) bilateral forepaw grasp, which measures the ability to hold onto a 2-mm-diameter steel rod, graded 0 for a rat with normal forepaw grasping behavior to 3 for a rat unable to grasp with the forepaws. The scores from all 4 tests are added and the average calculated to give a neurologic deficit score (maximum possible score, 3).

The EBST involves handling the animal by its tail and recording the direction of the swings. The animal is gently picked up at the base of the tail, and elevated by the tail until the animal's nose is at a height of 2 inches (5 cm) above the surface. The direction of the swing, either left or right, is counted once the animals head moves sideways approximately 10 degrees from the midline position of the body. After a single swing, the animal is placed back in the Plexiglas box and allowed to move freely for 30 seconds prior to retesting. These steps are repeated 20 times for each animal. Normally, intact rats display a 50% swing bias, that is, the same number of swings to the left and to the right. A 75% swing bias would indicate 15 swings in one direction and 5 in the other during 20 trials. We have previously utilized the EBST, and noted that MCAo stroke animals display >75% biased swing activity as early as the day of stroke surgery (i.e., after recovery from anesthesia), and such motor asymmetry is stable for up to six months (46, 50). All tests were conducted by two investigators blinded to the treatment condition.

FIG. 8 compares results for neurologic (Bederson test) and motor (EBST) evaluations prior to stroke surgery (pre-stroke), which revealed no detectable behavioral deficits between groups, and at 14 days after stroke (post-stroke). Post-stroke, while both groups exhibited motor and neurologic deficits (versus pre-stroke: *p's<0.05), the rats having Composition 1 supplementation exhibited significantly less motor and neurologic deficits than the control group (**p's<0.05). ANOVA statistical analysis revealed significant treatment effects in both Bederson ($F_{3,26}=81.65$, p<0.0001) and EBST ($F_{3,26}=29.26$, p<0.0001), as shown by the error bars displayed in FIG. 8. Pair-wise comparisons between treatment groups using Fisher's PLSD posthoc t-tests revealed Composition 1 supplementation and vehicle-treated groups displayed no detectable behavioral impairments at pre-stroke testing; however, both exhibited motor and neurologic deficits at post-stroke testing (compared to pre-stroke: p's<0.05). The rats having Composition 1-supplementation showed significantly improved motor and neurologic tests compared to the control group (at post-stroke testing: p's<0.05). Reductions of 11.8% and 24.4% in EBST motor asymmetry and Bederson neurologic dysfunction, respectively, were detected with Composition 1-supplementation compared to the control group.

Following the behavioral testing at day 14 post-stroke, all animals were euthanized for evaluation of cerebral infarction using the glial fibrillary acidic protein (GFAP) immuno-staining (Borlongan et al. 2000). The GFAP assay is a well accepted method to reveal the extent of any glial scar, which closely correlates with cerebral damage in stroke victims. Using an NIH imaging system, the glial scar was calculated by capturing images using AxioPhot (Carl Zeiss) at 1.6-fold magnification. The damaged area was selected according to the morphology of the cells based on glial infiltration which clearly delineated the ischemic core from the ischemic penumbra (Borlongan et al. 2000). The mean area of damage of 5-6 sections per coronal slice was calculated using the following formula: C=D/(A−B), to reveal the total infarct area per brain, with areas A, B, C and D being defined as shown in FIG. 9a, for example.

Figure 9:
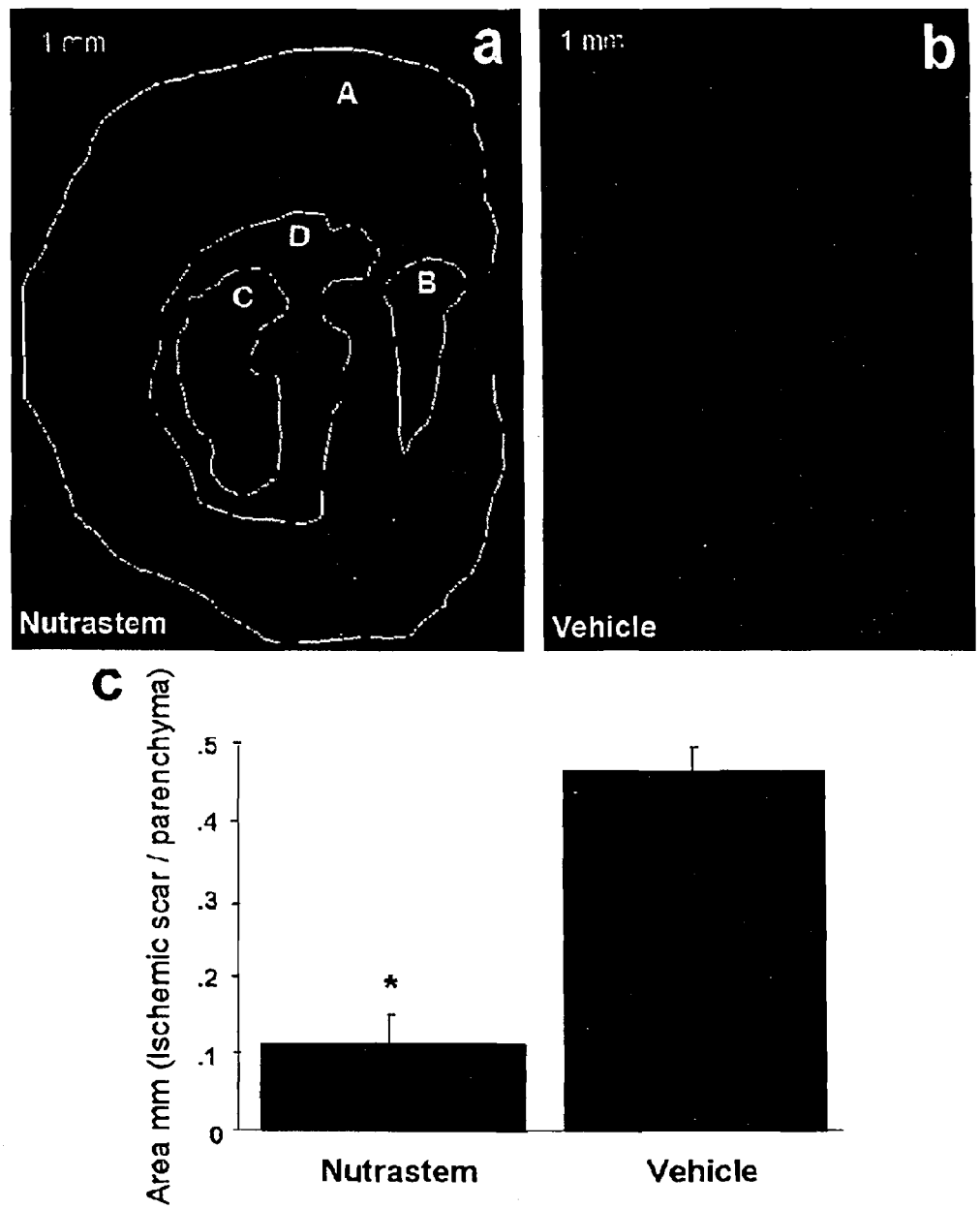

The t-test results of FIG. 9c show that Composition 1 supplementation reduces the glial scar/ischemic area damage in the striatum compared to the control group (Vehicle). A representative comparison is shown in the micrographs of FIG. 9a (Composition 2 supplementation) and FIG. 9b (Vehicle). A significant decrease in mean glial scar area (e.g. 75%) was observed in the ischemic striatum of animals having Composition 1 supplementation compared to that of vehicle-treated animals (p<0.0005) as shown by the error bars in FIG. 9c. These histological results parallel the improved behavioral performance for Composition 1 supplementation found in the Bederson Test and EBST.

The results that correlate Composition 1 supplementation to cell proliferation in vitro also occurs in vivo. It is believed, without being limiting, that stem cell proliferation serves as the mechanistic explanation for the observed improvements in behavioral and histological observations for induced stroke animals compared to the control group. Alternate brain sections obtained from the same Composition 1 supplementation or control animals were processed for BrdU immunostaining (Sigma, 50 mg/kg, i.p. every 8 hours during days 10 to 14 post-stroke) to reveal cell proliferation. Analyses of BrdU labeling were focused at the neurogenic subventricular zone (SVZ) and the non-neurogenic striatum. Focusing on SVZ is used to reveal any effect of Composition 1 supplementation on increased cell proliferation in a neurogenic site. An increased cell proliferation in SVZ may be used to show support of a mechanism for neuro-protection using Composition 1 supplementation. In addition, Analyzing BrdU labeling in the ischemic striatum reveals whether newly formed cells from the SVZ are able to migrate towards the site of an induced-stroke injury. Evidence of migration of newly proliferated stem cells to a site of injury provides the strongest possible evidence for the efficacy of Composition 1 supplementation in the mechanism responsible for protection from induced-stroke damage.

Figure 10:
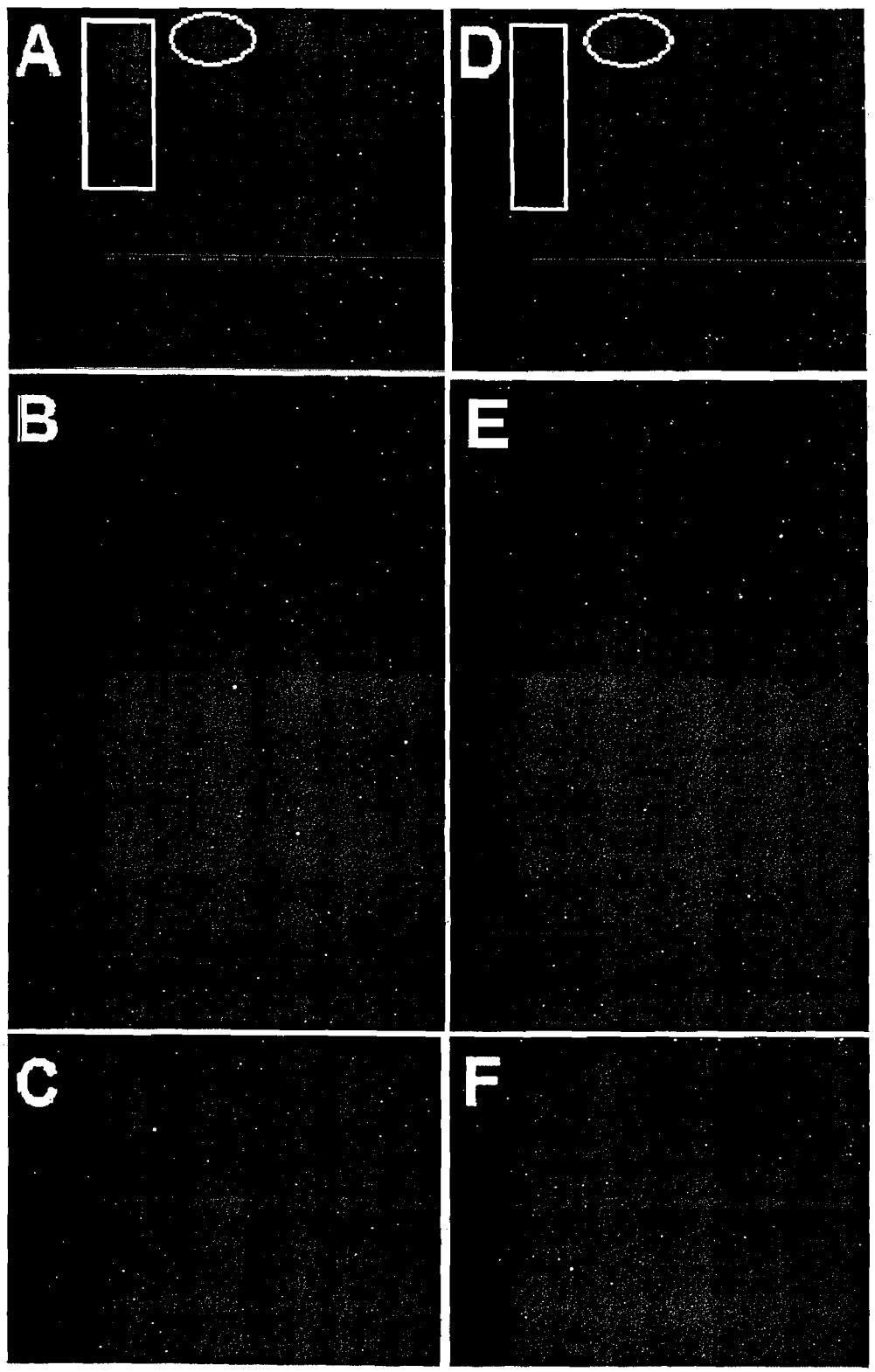

The images of FIG. 10 A-F show BrdU labeling of brain tissues. Immunofluorescence microscopy was used to visualize cell proliferation in SVZ and ischemic striatum of animals given Composition 1 supplementation compared to a control group. FIG. 10 D-F were taken from animals given Composition 1 supplementation. These micrographs are characterized by significantly increased BrdU labeling in both SVZ and ischemic striatum of brain sites compared to the BrdU labeling of the same brain sites of animals in the control group, which are shown in FIG. 10 A-C. Composition 1 increased the number of BrdU-positive proliferating cells in SVZ (panel D in rectangle and magnified in E) and ischemic striatum (panel D in circle and magnified in F) compared to vehicle treatment (SVZ: panel A in rectangle and magnified in B; striatum: panel A in circle and magnified in C).

Figure 12:
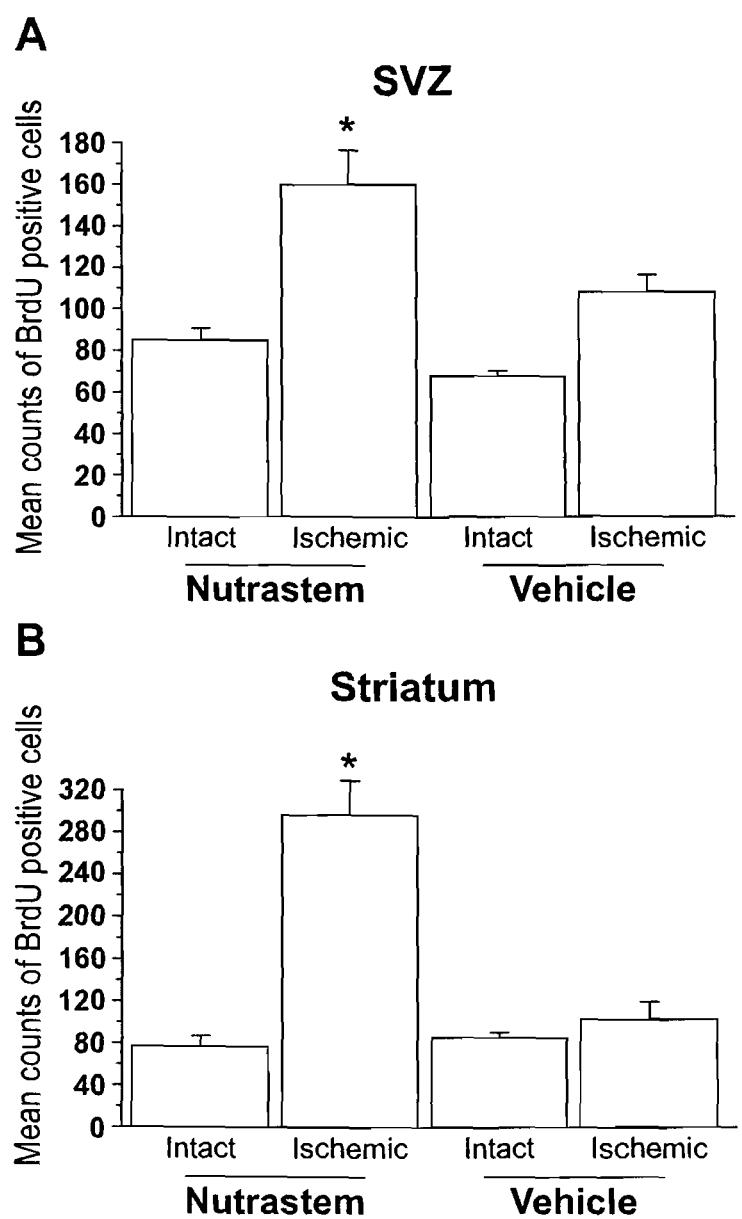

In FIG. 12 quantitative analysis of SVZ's cell proliferative activity, as shown in the micrograph of FIG. 11 (protocol based on Baldauf and Reymann, 2005) revealed significant treatment effects ($F_{3,16}=18.03$, p<0.0001), with at least a one-fold increment in the number of BrdU-positive cells in the Composition 1 supplementation stroke brains compared to control stroke brains (p<0.0005) (FIG. 10 A,D in rectangles and magnified in B,E; quantitative data shown in FIG. 12 A). Similarly, quantitative analysis of BrdU labeling in the ischemic striatal penumbra revealed significant treatment effects ($F_{3,16}=11.84$, p<0.0001), with at least a three-fold increase in the number of BrdU-positive cells in the Composition 1 treated stroke brains compared to vehicle-treated stroke brains (p<0.0001) (FIG. 10 A,D in circles and magnified in C,F; quantitative data shown in FIG. 12 B). In contrast, when evaluation of BrdU labeling targeted the ischemic core (instead of the penumbra, see FIG. 1 A,D), there was a massive proliferation of BrdU-positive cells in the vehicle-treated stroke brains compared to Composition 1 treated stroke brains. This apparent increase in BrdU labeling in the vehicle-treated ischemic core might be misunderstood as a sign of proliferation, but may be understood as being established by BrdU labels infiltrating reactive microglia, as well as degenerating or dead cells which are abundant in the necrotic core (Borlongan et al. 2000; Ito et al. 2001; Beech et al. 2001; Marks et al. 2001). Since Composition 1 treated stroke brains have smaller ischemic core, it is expected that BrdU labeling in this region is less than that of the vehicle-treated stroke brains. Accordingly, examination of cell proliferation in the ischemic core is known to present as an artifact that might not truly reflect a neuroprotective BrdU labeling index. With this in mind, the evaluation of cell proliferation is limited to SVZ and ischemic penumbra, which are not known to present as an artifact. Both these sets of data indicate that Composition 1 increases cell proliferation in the neurogenic SVZ, and also facilitated the migration of these newly formed cells towards the ischemic striatal penumbra. Quantitative analysis of BrdU labeling in SVZ followed the protocol by Baldauf and Reymann (2005). Four rectangular sections (200 um×60 um) at 100× magnification from two serial brain sections from each rat were used to reveal mean BrdU cell counts along the SVZ. For quantitative analysis of BrdU labeling in striatum, two serial brain sections from each rat capturing the striatal penumbra depicted in FIG. 10 A,D (magnified in FIG. 5 C,E), with each section corresponding to 40 um×40 um, were used to reveal mean BrdU cell counts in the ischemic striatum. Results revealed one-fold and three-fold increments, respectively, in the SVZ results of FIG. 12 A and striatum results of FIG. 12 C for the Composition 1 treated stroke brains compared to vehicle-treated stroke brains (*p<0.0005 in SVZ and *p<0.0001 in striatum when comparing corresponding ischemic SVZs and striata between treatment groups).

Composition 1 leads to increased expression of neuronal phenotypes, bolstering the evidence of a mechanism of neurogenesis underlying Composition 1 neuro-protection. The BrdU-labeled brain sections (i.e., ischemic striatal penumbra) used for cell migration studies above were also labeled with the neuronal marker doublecortin or glial marker GFAP. Composition 1 enhanced neuronal differentiation of newly formed cells in the ischemic striatum is revealed by a high number of BrdU (D) and doublecortin (E) double-labeled cells (F) compared to vehicle treatment (A: BrdU, B: doublecortin, C: merged). Immunofluorescence microscopy revealed widespread double-labeling of cells with BrdU and doublecortin in Composition 1 treated stroke brains (FIG. 13D-F). In contrast, only a few cells double-labeled with both BrdU and doublecortin in vehicle-treated stroke brains (FIG. 13A-C).

Quantitative analysis revealed significantly higher double-labeling of BrdU and doublecortin in Composition 1 than vehicle-treated stroke brains (*p<0.05, p<0.0001) of FIG. 14 A. In contrast, there were significantly lower BrdU and GFAP double-labeling in Composition 1 than vehicle-treated stroke brains (p's<0.0001) of FIG. 14 B. Quantitative analysis revealed about 17% and 75% double-labeling of BrdU and doublecortin in respective intact and infarcted side of Composition 1 treated stroke brains, which were significantly higher than those seen in the intact (5%) and infarcted side (13%) of vehicle-treated stroke brains (*p<0.05, **p<0.0001) as shown in FIG. 14A.

In contrast, only a few cells in Composition 1 treated stroke brains double-labeled with BrdU and GFAP (FIG. 15D-F), while many cells in vehicle-treated stroke brains double-labeled with BrdU and GFAP (FIG. 15A-C). The GFAP marker differentiates glial lineage. In FIG. 15A-F, Composition 1 supplementation did not enhance differentiation of newly formed cells into glial lineage in the ischemic striatum, as revealed by a few cells with BrdU (D) and GFAP (E) double-labeling (F), while cells reveal double-labeling with BrdU and GFAP in the vehicle treated ischemic striatum (A: BrdU, GFAP, C: merged).

Quantitative analysis revealed about 1% and 2% double-labeling of BrdU and GFAP in respective intact and infarcted side of Composition 1 treated stroke brains. The analysis of intact (18%) and infarcted (35%) sides of vehicle-treated stroke brains showed significantly higher double-labeling (**p's<0.0001) (FIG. 9B). These data show that Composition 1 induces neural differentiation, with increased tendency towards neuronal over glial lineage.

The pathological manifestation of stroke, at least in this MCAo model, is characterized by extensive neuronal loss accompanied by increased glial cell activation. Thus, it appears that the neuronal replacement provided by the Composition 1 supplement is more beneficial than the glial cell replenishment occurring in the control group, given the vehicle-only treatment. The robust neuronal differentiation at two weeks post-stroke is equally advantageous since a rapid cell death cascade proceeds after the stroke onset. The preferential neuronal differentiation during the acute stroke phase provides a solid evidence that neurogenesis plays a major active role in the Composition 1 mediated neuro-protection. Thus, it is believed that there are multiple advantages to using supplementation effective in repairing damage caused by injuries such as stroke in mammals.

Many other combinations and doses will be apparent to an artisan based on the examples and ranges provided for combinations of ingredients. Some synergistic effects are shown for combinations of two or more of the listed active ingredients. In a composition preferred for protective effect from injury and proliferation and differentiation of stem cells, as shown by in vivo and in vitro results, three or more substances are compounded in effective, synergistic ratios of blueberry, carnosine, green tea extract and Vitamin D3, with or without equivalent amounts of VitaBlue, catechins or other substances. Ranges of effective doses may be tailored for a specific mammal by comparing the amount of each substance measured in blood serum levels, as compared to a known animal or human.

What is claimed is:

1. A composition for stimulation of stem cell proliferation comprising 400 mg to 25 grams of blueberry extract, 10 mg to 100 mg of carnosine, and 400 mg to 5 grams of green tea extract.

2. The composition of claim 1, wherein the composition further comprises vitamin $D_3$.

3. A method for increasing stem cell proliferation comprising orally administering a composition comprising 400 mg to 25 grams of blueberry extract, 10 mg to about 100 mg of carnosine, and about 400 mg to 5 grams of green tea extract to a human.

4. The method of claim 3, wherein the composition further comprises vitamin $D_3$.

* * * * *